(12) United States Patent
Garrahy et al.

(10) Patent No.: US 12,313,586 B2
(45) Date of Patent: May 27, 2025

(54) SENSING ELEMENT FOR USE WITH MEDIA-PRESERVING STORAGE AND CALIBRATION CHAMBER

(71) Applicant: Broadley-James Corporation, Irvine, CA (US)

(72) Inventors: Robert J. Garrahy, Laguna Niguel, CA (US); Scott T. Broadley, Laguna Beach, CA (US); Chang-Dong Feng, Long Beach, CA (US); Bradley Joseph Sargent, Mission Viejo, CA (US); Josh L. Rothman, North Tustin, CA (US); Andrew John Boyce, Irvine, CA (US)

(73) Assignee: Broadley-James Corporation, Irvine, CA (US)

( * ) Notice: Subject to any disclaimer, the term of this patent is extended or adjusted under 35 U.S.C. 154(b) by 894 days.

(21) Appl. No.: 16/649,353

(22) PCT Filed: Sep. 21, 2018

(86) PCT No.: PCT/US2018/052290
§ 371 (c)(1),
(2) Date: Mar. 20, 2020

(87) PCT Pub. No.: WO2019/060776
PCT Pub. Date: Mar. 28, 2019

(65) Prior Publication Data
US 2020/0217817 A1    Jul. 9, 2020

Related U.S. Application Data

(60) Provisional application No. 62/562,260, filed on Sep. 22, 2017.

(51) Int. Cl.
*G01N 27/28* (2006.01)
*C12M 1/00* (2006.01)
(Continued)

(52) U.S. Cl.
CPC .......... *G01N 27/4165* (2013.01); *C12M 1/34* (2013.01); *C12M 23/28* (2013.01); *C12M 41/26* (2013.01); *G01N 27/283* (2013.01)

(58) Field of Classification Search
CPC ................................... G01N 27/283
See application file for complete search history.

(56) References Cited

U.S. PATENT DOCUMENTS

| 5,011,587 A | 4/1991 | Schmidt |
| 5,711,863 A | 1/1998 | Henkelmann et al. |

(Continued)

FOREIGN PATENT DOCUMENTS

| CH | 698228 B1 | 12/2012 |
| DE | 19721965 A1 | 12/1997 |

(Continued)

OTHER PUBLICATIONS

International Search Report and Written Opinion dated Feb. 6, 2019 for Application No. PCT/US2018/052290.

(Continued)

*Primary Examiner* — Jonathan M Hurst
(74) *Attorney, Agent, or Firm* — Knobbe, Martens, Olson & Bear, LLP

(57) ABSTRACT

A sensor may include a sensing element retained within a storage compartment filled with a storage medium, which may also be used as a calibration medium. The sensing element can include a sensing surface located away from the distal end of the sensing element, such that an inactive section of the sensing element can cooperate with a sealing member such as an O-ring to form part of the seal retaining the storage/calibration medium. The sensing element can be extended and retracted from the storage compartment to expose the sensing surface to a process medium, while (Continued)

preserving the storage medium within the storage compartment for post-measurement validation.

19 Claims, 27 Drawing Sheets

(51) Int. Cl.
*C12M 1/34* (2006.01)
*G01N 27/416* (2006.01)

(56) References Cited

U.S. PATENT DOCUMENTS

| | | | |
|---|---|---|---|
| 5,939,610 A | 8/1999 | Iwamoto et al. | |
| 7,272,983 B2 | 9/2007 | Caderas | |
| 7,325,555 B2 | 2/2008 | Caderas | |
| 7,594,449 B2 | 9/2009 | Tottewitz et al. | |
| 7,806,009 B2 | 10/2010 | Tottewitz et al. | |
| 7,967,963 B2 | 6/2011 | Uthemann et al. | |
| 8,578,798 B2 | 11/2013 | Pfauch et al. | |
| 10,036,718 B2 | 7/2018 | Yamanouchi | |
| 10,436,736 B2 | 10/2019 | Kohlmann | |
| 10,598,626 B2 | 3/2020 | Wunderlich et al. | |
| 10,705,044 B2 | 7/2020 | Hanko et al. | |
| 2003/0019308 A1 | 1/2003 | Oppermann et al. | |
| 2009/0032397 A1* | 2/2009 | Woodward | G01N 27/36 |
| | | | 204/416 |
| 2009/0214387 A1* | 8/2009 | Straub | G01N 27/283 |
| | | | 422/82.01 |
| 2010/0045312 A1 | 2/2010 | Pechstein et al. | |
| 2010/0109882 A1* | 5/2010 | Lohmann | G01N 27/286 |
| | | | 324/438 |
| 2011/0236962 A1* | 9/2011 | Loebbert | C12M 41/26 |
| | | | 73/1.03 |
| 2011/0290045 A1† | 12/2011 | Hanko | |
| 2012/0144894 A1 | 6/2012 | Trapp et al. | |
| 2017/0089740 A1 | 3/2017 | Wunderlich et al. | |
| 2017/0138896 A1 | 5/2017 | Ito | |
| 2017/0219512 A1† | 8/2017 | Wunderlich | |
| 2018/0172615 A1 | 6/2018 | Lau | |

FOREIGN PATENT DOCUMENTS

| | | | |
|---|---|---|---|
| DE | 19961210 A1 | 6/2001 | |
| DE | 102 41 834 A1 | 9/2002 | |
| DE | 19720504 B4 | 7/2005 | |
| DE | 10 2005 051 279 A1 | 10/2005 | |
| DE | 102007030584 B4 | 5/2009 | |
| DE | 10 2010 001 779 A1 | 2/2010 | |
| DE | 102006048898 B4 | 9/2010 | |
| DE | 20 2012 002 473 U1 | 5/2012 | |
| DE | 102014101759 A1 | 8/2015 | |
| DE | 10 2016 101 715 A1 | 2/2016 | |
| EP | 0151285 A2 | 8/1985 | |
| EP | 0372121 B1 | 3/1992 | |
| EP | 0590290 A1 | 4/1994 | |
| EP | 1148317 A2 | 10/2001 | |
| EP | 1 752 763 A1 | 2/2007 | |
| EP | 1832871 A2 | 9/2007 | |
| EP | 2071325 A2 | 6/2009 | |
| EP | 2278312 B1 | 3/2014 | |
| JP | 1164178 A | 3/1999 | |
| KR | 101485834 B1 | 1/2015 | |
| WO | WO 1991005248 A1 | 4/1991 | |
| WO | WO 2003036283 A2 | 5/2003 | |
| WO | WO 2004011934 A1 | 2/2004 | |
| WO | WO 2016/172507 A1 | 10/2016 | |

OTHER PUBLICATIONS

Notices of Opposition dated Nov. 8, 2024 for European Application No. 18796151.1.

\* cited by examiner
† cited by third party

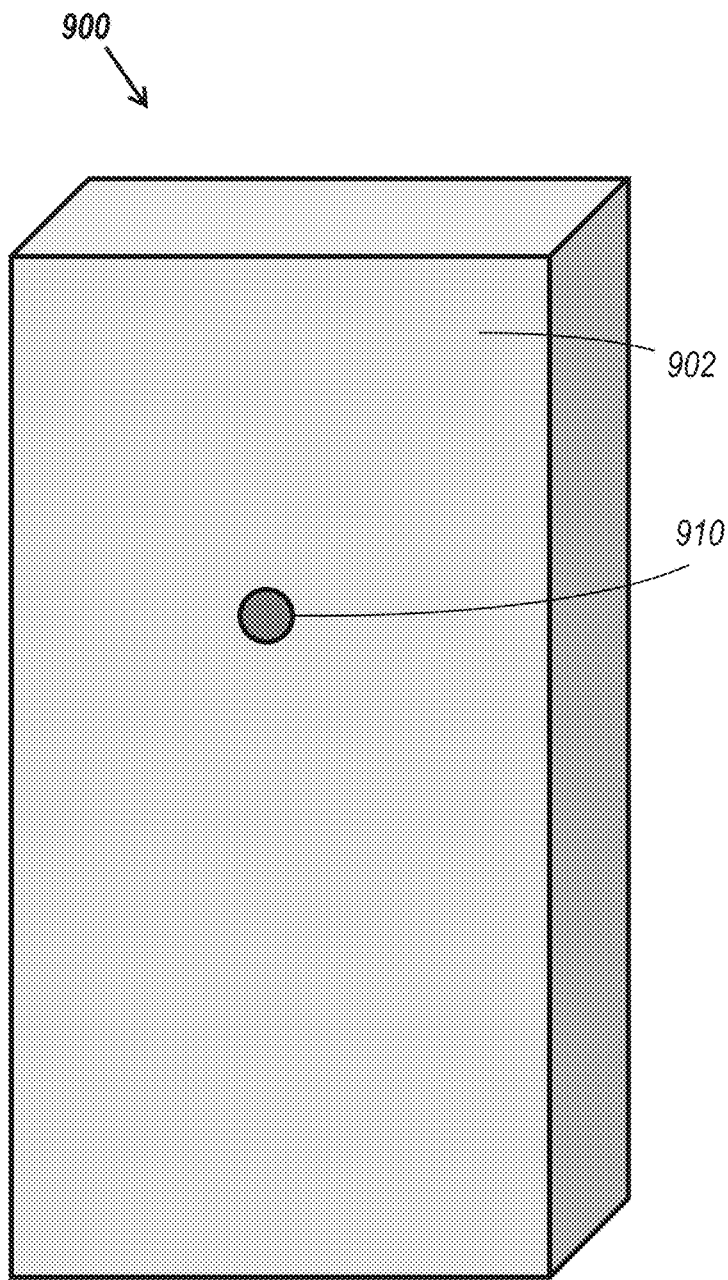
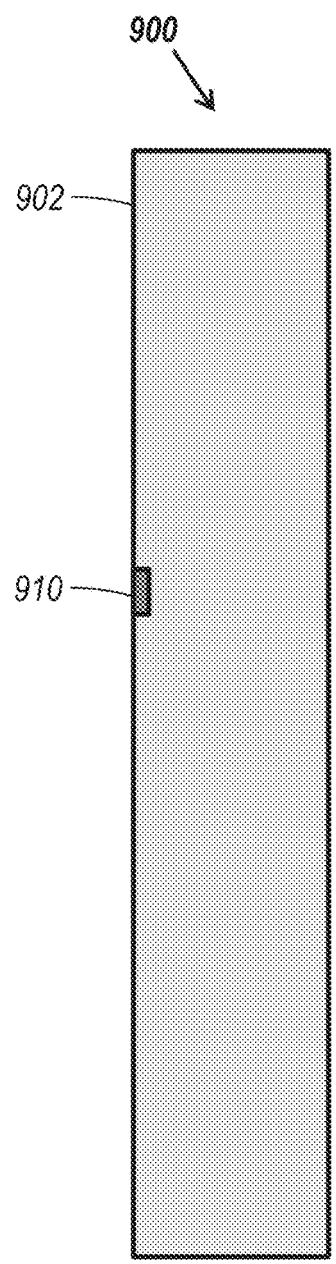
FIG. 9A
FIG. 9B

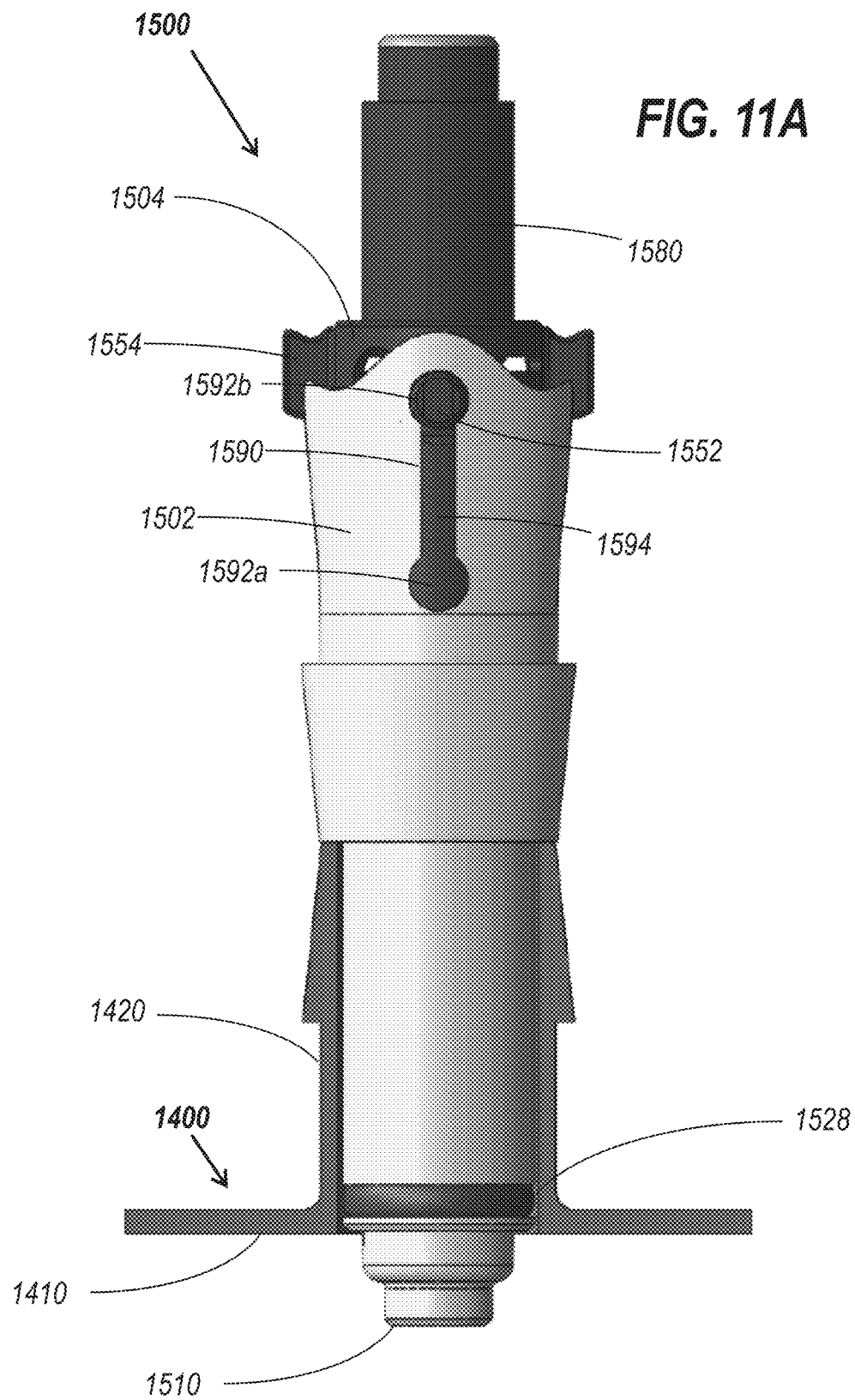

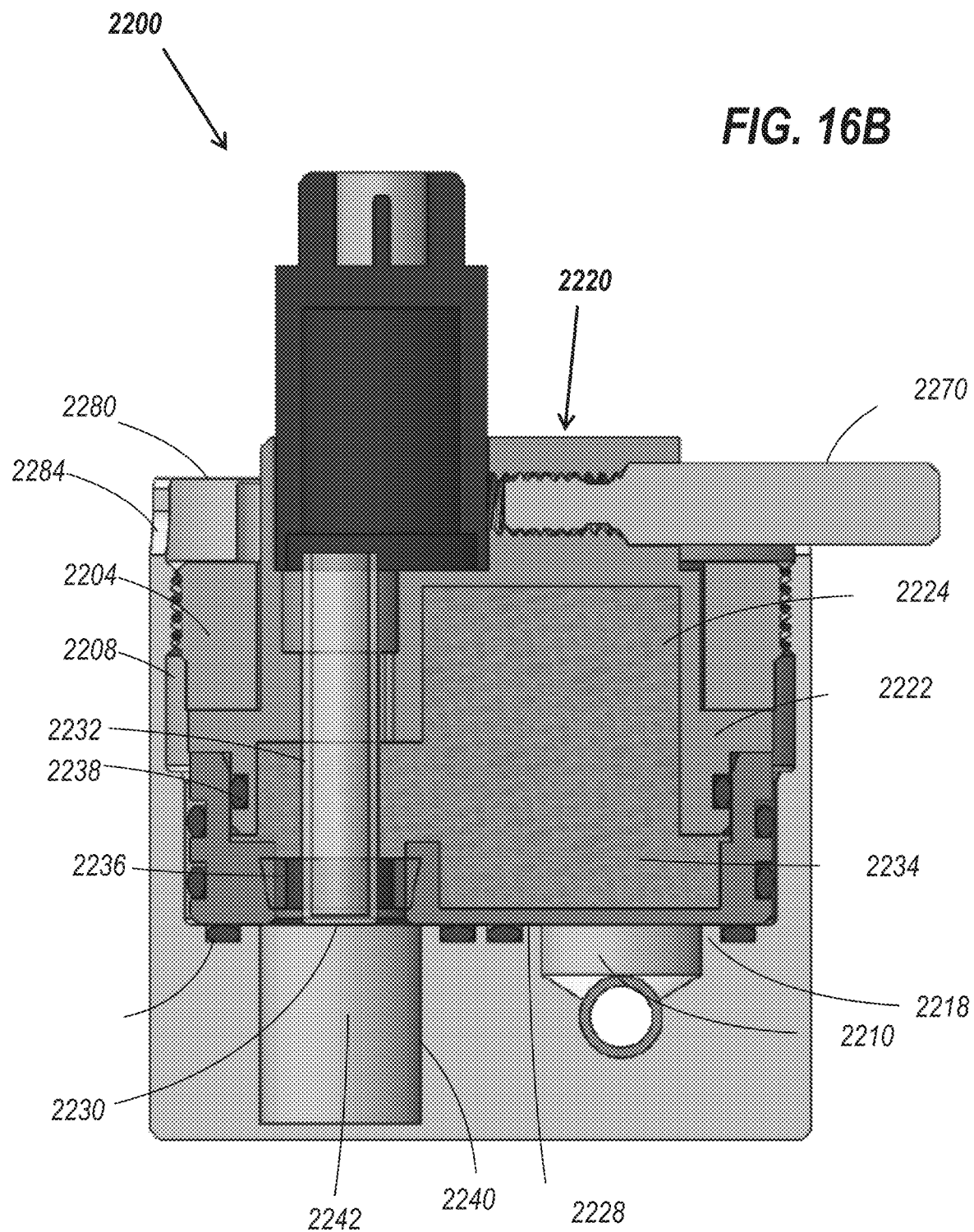

SENSING ELEMENT FOR USE WITH MEDIA-PRESERVING STORAGE AND CALIBRATION CHAMBER

BACKGROUND

Technical Field

Embodiments described herein relate to sensor systems and associated devices, and in particular to sensor systems including integrated storage and calibration compartments.

Description of the Related Art

In biopharmaceutical manufacturing processes, the use of single-use measurement systems pushes the responsibility of cleaning, sterilization, and validation processes to the system vendors, increases the speed and flexibility of the manufacturing process and reduces the capital investment for system users who are the biopharmaceutical manufacturers.

With single-use systems, sensors such as pH and dissolved oxygen (DO) sensors can be integrated into a system such as a single-use bioreactor bag, or elsewhere in a process flow. The final system product can then go through a gamma irradiation process for the sterilization of the system and be shipped to the end user customer. At the end user site, the pH sensors on the system are not accessible to the operator for a standard calibration process without breaching the sterility of the bioreactor bag or other structure. However, an on-site calibration and/or validation of the sensors may nevertheless be required before a manufacturing process, such as a cell culture, begins. After the manufacturing process, an additional post-measurement validation of the sensors may also be required.

SUMMARY

In one embodiment, a sensor structure is provided, including a storage compartment configured to retain a storage medium therein, a sensing element extending through an aperture in the compartment and including a sensing structure, a distal end of the sensing structure located proximal a distal end of the sensing element, the sensing element movable between a first position in which the sensing structure is in fluid communication within the storage compartment and a second position in which the sensing structure is not in fluid communication with the storage compartment, and a sealing element disposed at least partially within the aperture and configured to engage a surface of the sensing element to provide a seal inhibiting fluid flow in or out of storage compartment through the aperture.

The sensing surface can be substantially flush with the adjacent surfaces of the sensing element. The sensing element can include a section of substantially constant cross-sectional shape extending between a point distal the proximal end of the sensing surface and a point proximal the distal end of the sensing surface. The sensing surface can form at least part of an outer surface of a cylindrical section of the sensing element. A shape of the surface of the sensing element in contact with the sealing element can remain substantially constant during movement of the sensing element from the first position to the second position.

The sealing element can include a gasket. The sealing element can include an O-ring. The sealing element can include a resilient material. The sensing element can include a pH probe. The sensing structure can include a glass electrode. The sensing structure can be in electrical communication with a reference electrode.

The storage medium can be configured to be used as a calibration medium for the sensing element. The storage solution can have a pH of less than 6.0, less than 5.0, or less than 4.0. The storage solution can have a pH of between 0 and 14, between 1 and 13, between 3 and 12, between 4 and 10.5, between 5 and 10.5, or between 6 and 10.5.

Translating the sensing element between the first position and the second position can, in some embodiments, not displace a substantial amount of the storage solution from the storage compartment. Translating the sensing element between the first position and the second position can, in some embodiments, not expose the interior of the storage compartment. The translating the sensing element between the first position and the second position can displace less than 90% pf the storage solution from the storage compartment, less than 50% of the storage solution from the storage compartment, less than 10% of the storage solution from the storage compartment, 5% of the storage solution from the storage compartment, or less than 3% of the storage solution from the storage compartment, or less than 1% of the storage solution from the storage compartment.

The sensor structure can additionally include a second sensing element extending parallel to the first sensing element, where the second sensing element extends through a second aperture in the storage compartment and engages with a second sealing element disposed at least partially within the second aperture to provide a seal inhibiting fluid flow in or out of storage compartment through the second aperture. The storage compartment can include a first chamber and a second chamber, the sensing element extending through both the first chamber and the second chamber, where the sensing structure of the sensing element is within the first chamber when the sensing element is in the first position, and where the sensing element is longitudinally translatable to a third position in which the sensing structure is located within the second chamber. The first chamber can retain the storage solution, and the second chamber can retain a calibration medium, the calibration medium having a pH which is different from the pH of the storage solution.

In another embodiment, a method is disclosed of measuring a property of a process medium using a sensor system including a storage compartment configured to retain a storage solution therein, and a sensing element extending through an aperture in the compartment and including a sensing structure, a distal end of the sensing structure located proximal a distal end of the sensing element, the sensing element longitudinally translatable between a first position in which the sensing structure is located within the storage compartment and a second position in which the sensing structure is located outside the storage compartment, the method including recording a first measurement when the sensing element is in a first position in which the sensing structure of the sensing element is positioned outside of the storage compartment and exposed to the process medium, moving the sensing element from the first position to a second position in which the sensing structure of the sensing element is positioned within or otherwise exposed to the storage compartment, and recording a second measurement when the sensing element is in the second position. The method can additionally include, prior to recording the first measurement when the sensing element is in the first position recording an initial measurement when the sensing element is in an initial position in which the sensing structure of the sensing element is positioned within the storage compartment and exposed to the storage solution, and longitudinally translating the sensing element from the initial position to the first position.

In another embodiment, a single-use bioreactor component is provided, including a process chamber configured to retain a process medium within an interior of the chamber, a storage compartment secured relative to the chamber, the storage compartment including an aperture extending between an interior chamber of the storage compartment and the process chamber, the storage compartment including a storage and calibration medium within the interior chamber of the storage compartment, a sensing structure extending through at least a portion of the storage compartment and into the interior of the process chamber, the sensing structure including a sensing surface exposed to the storage and calibration medium within the storage compartment, and a sealing structure disposed adjacent or within the aperture extending between an interior chamber of the storage compartment and the process chamber, the sealing structure cooperating with an inactive portion of the sensing structure to form a seal inhibiting flow of the storage and calibration medium through the aperture, The interior of the process chamber and the interior chamber of the storage chamber can form part of a sealed and sterilized portion of the single-use bioreactor component. The process chamber can include a single-use bioreactor bag. The process chamber can include a fluid channel configured to be placed in communication with a bioreactor chamber. The sensing structure can be configured to be moved between a first position in which the sensing surface is exposed to the storage and calibration medium within the storage compartment, and a second position in which the sensing surface is exposed to the interior of the process chamber, and the sealing structure can be configured to maintain the seal inhibiting flow of the storage and calibration medium through the aperture during movement of the sensing structure between the first position and the second position. A shape of the surface of the portion of the sensing element in contact with the sealing element can remain substantially constant during movement of the sensing element from the first position to the second position. The single-use bioreactor component can additionally include at least one sterile port in communication with the interior chamber of the storage compartment to allow access to the storage and calibration medium without compromising the sterility of the single-use bioreactor component.

In another embodiment, a single-use bioreactor component is provided, including a process compartment configured to retain a process medium therein, a storage compartment including an aperture extending therethrough, the storage compartment containing a calibration medium, a sensing structure, where a first portion of the sensing structure is in fluid communication with the process compartment, and where a second portion of the sensing structure is in fluid communication with the storage compartment, the second portion of the sensing structure including a sensing surface, and a sealing structure disposed adjacent or within the aperture in the storage compartment, the sealing structure cooperating with a portion of the sensing structure to form a seal inhibiting flow of the calibration medium through the aperture.

The sensing structure can be configured to be moved between a first position in which the first portion of the sensing structure is in fluid communication with the process compartment, and a second position in which at least part of the second portion of the sensing structure is in fluid communication with the storage compartment to expose the sensing surface to the process compartment. The sealing structure can be configured to maintain the seal inhibiting flow of the storage and calibration medium through the aperture during movement of the sensing structure between the first position and the second position. The sensing structure can be rotated between the first position and the second position. The sensing structure can be translated between the first position and the second position. A surface profile of the portion of the sensing element in contact with the sealing element can remain substantially constant during movement of the sensing structure from the first position to the second position.

BRIEF DESCRIPTION OF THE DRAWINGS

FIG. 9A is a perspective view schematically illustrating another embodiment of a sensing element. FIG. 9B is a side view schematically illustrating the sensing element of FIG. 9A.

FIG. 11A is a side view of another embodiment of a sensor structure including a sensing element such as the sensing element of FIG. 2 and a storage compartment containing a calibration solution, shown inserted into a tube port.

FIG. 16B is a side cross-sectional view of the sensor structure of FIG. 16A, with the sensor shown in a position in which the sensing element is exposed to calibration solution.

DETAILED DESCRIPTION

Figure 1:
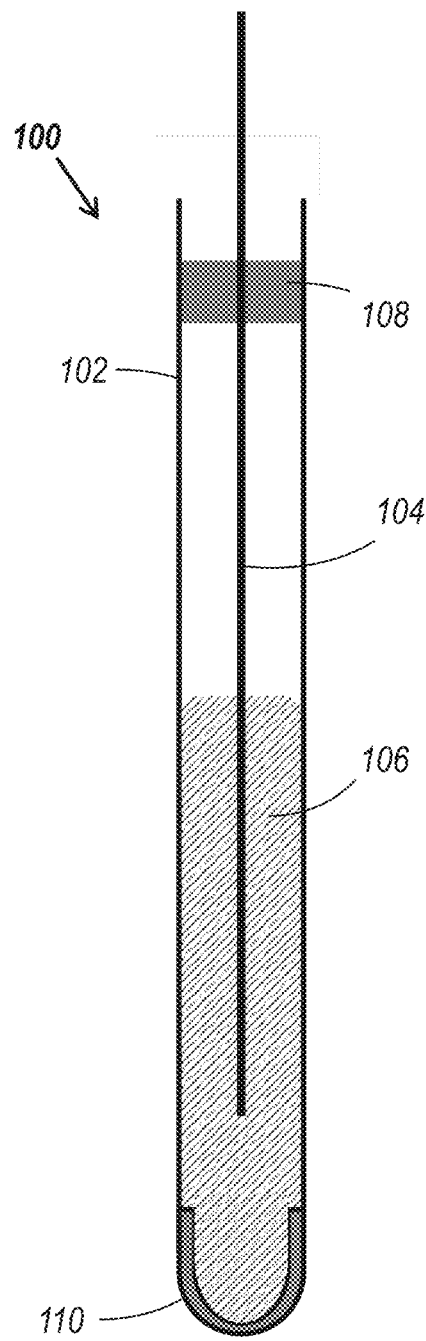
FIG. 1 is a side cross-sectional view schematically illustrating an embodiment of a pH sensing element.

FIG. 1 is a side cross-sectional view schematically illustrating a pH sensing element. The sensing element 100, which may be a pH glass electrode, includes a body 102 having a half-cell element lead 104 and an internal electrolyte 106 retained within a hollow space within the body 102, and sealed in place by a seal 108. The sensing element 100 may also include or be in electrical communication with a reference electrode (not shown).

The distal end of the sensing element 100 includes a pH sensing glass electrode 110, which serves as a sensing surface of the sensing element 100. In some embodiments, this glass electrode 110 can be formed by being blown into a bulb shape at the end of the electrode stem glass tubing. By immersing the sensing element into a process medium or other medium to be measured, such that the sensing surface of the sensing element is immersed in the process medium, a voltage indicative of the pH of the process medium can be measured.

In some embodiments, a measurement of a process medium retained in a bioreactor can be made. In some embodiments, a bioreactor can include rigid walls, and a sensor can be configured such that a sensing element can be inserted through a port in the rigid wall of the bioreactor, with the rigidity of the bioreactor wall providing mechanical support for a variety of different structures or mechanisms used to selectively expose a probe to the process medium therein.

In other embodiments, however, the bioreactor can include a bag or other flexible structure, which is filled with and retains the process medium. Such a flexible bioreactor may itself be seated within a rigid retaining vessel, but as the walls of the actual containment vessel retaining the process medium are flexible, probes and other components which are configured to be insertable through or otherwise extend through the wall of the flexible bioreactor.

For example, such components may be configured to be insertable through reinforced ports in the flexible bioreactor wall, such that the sterility and integrity of the flexible bioreactor are not compromised during the insertion process. In some embodiments, sensors may be built into the flexible bioreactor bag prior to the bioreactor being sterilized or filled with a process medium, or otherwise installed prior to the flexible bioreactor being sterilized. Other components, such as agitators, may be similarly insertable through ports in the flexible bioreactor, or may be provided within the bioreactor prior to sterilization and/or filling of the bioreactor with sterile components or media. Because of manner in which a flexible bioreactor such as a flexible single-use bioreactor are manufactured, the sensor or other components of the single-use bioreactor may not be easily accessible to the end user for the purposes of calibration or performance verification, as they cannot be removed or retracted without breaching the sterile barrier.

In some embodiments, a sensor can include a storage compartment or chamber surrounding at least a portion of the sensing element therein, where the sensing surface at the distal end of a sensing element is stored within a storage medium. Storage of the sensing surface of the sensing element, along with other components of the sensor such as a reference electrode, may be used to enable deployment of the sensor on-demand, without the need to wet the sensing surface for a period of time before measurements can be taken. In some embodiments, the storage medium may also be used as a calibration solution, by using the sensor to take a measurement of the known pH of the storage medium prior to deployment of the sensing element into the process medium. This can allow calibration of the sensor even when the sensor is stored within the sealed storage compartment, and inaccessible to the end user. In some embodiments, a significant period of time may elapse between the time at which the sensor is sealed into or relative to the sterile environment of a single-use bioreactor bag or component to be used with such a single-use bioreactor bag, sometimes on the order of several years. On-site calibration prior to use of the sensor can be needed to ensure that an accurate measurement can be obtained using the sensor.

When a measurement of the process medium is desired, the sensing element can be pushed into the process medium, immersing the sensing surface and reference electrode of the sensor into the process medium. In doing so, because the sensing surface of the sensing element is located at the distal end of the sensing element, the storage solution is exposed to the process medium, so that any fluid remaining in the storage chamber is intermixed with the process medium. As the storage chamber can be substantially smaller than the volume of the process medium, the storage medium will be dispersed into the process medium, and the fluid remaining within the storage chamber, if any, will be substantially the same composition and pH of the process medium.

Figure 2:
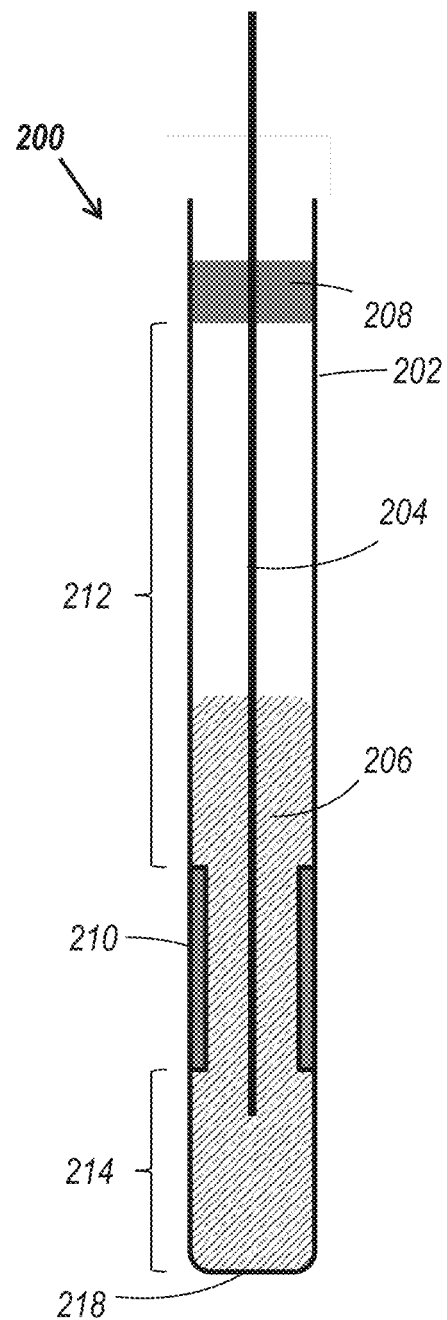
FIG. 2 is a side cross-sectional view schematically illustrating an embodiment of a pH sensing element including a sensing structure located at a point located away from the end of the structure.

In some embodiments, an alternative sensing element design may be used, and the alternative sensing element design may enable a variety of different single-use sensor designs. FIG. 2 is a side cross-sectional view schematically illustrating a pH sensing element including a sensing structure located at a point located away from the end of the structure. The sensing element 200 is similar to the sensing element 100 of FIG. 1, including a body 202 having a hollow space therein, in which a half-cell element lead 204 and an internal electrolyte 206 are located, and a seal 208 retained those components within that hollow space. However, the sensing element 200 differs in that the sensing surface 210, which as discussed above may be a glass pH electrode, is located at a point away from the very distal end 218 of the sensing element 200.

In particular, it can be seen that the sensing element 200 includes a proximal portion 212, whose outer surface does not contain a sensing surface 210, as well as a distal portion 214 which also does not contain a sensing surface 210. The sections of the sensing element 200 which do not contain a sensing surface 210, liquid junction, or similar component, may be referred to herein as inactive portions of the sensing element. The sensing surface 210 may comprise, for example, a cylindrical outer section of the body 202 of the sensing element 200, but need not extend around the entire outer perimeter of the body 202. For example, in some embodiments, the sensing surface 210 may be a section of a glass pH electrode or other suitable sensing surface in any desired shape.

In other embodiments, the sensing surface 210 may comprise glass, metal, electronic components, or any other suitable sensing structure. In some embodiments, the sensing surface 210 may comprise semiconductor components, such as thermistors and resistors, or may comprise integrated circuits such as ion-sensitive field-effect transistors (ISFETs). The sensing element 200 may be a part of any sensor, including sensors that reference voltage, current, capacitance, resistance, frequency, or luminescence. Although many embodiments herein are described in the context of pH sensors which can be used with single-use flexible bioreactor bags, embodiments of sensing elements and other components described herein can also be used in a wide range of other sensor types and applications.

The body 202 can be any suitable shape. However, in some embodiments, the body 202 may include a section of substantially constant cross-section extending at least from a point proximal the proximal end of the sensing surface 210, within the proximal section 212 of the sensing element 200, to a point distal the distal end of the sensing surface 210, within the distal section 214. When viewed in cross-section, it can be seen that the outer surface of the sensing surface 210 is substantially coplanar with the adjacent proximal and distal sections 212 and 214 of the sensing element 200. As described in greater detail below, such a sensing element 200 can be translated in the direction of its longitudinal axis, relative to a storage chamber, while minimizing fluid flow into or out of the storage chamber.

A sensor including the sensing element 200 may also include additional components not specifically illustrated in FIG. 2. For example, the sensor may include a reference electrode which may in some embodiments be integrated within the structure of the sensing element 200 (see, for example, FIGS. 4A and 4B). In other embodiments, described in more detail with respect to FIG. 6, a reference electrode may be located within a separate structure, which may in some embodiments extend along a parallel longitudinal axis to the longitudinal axis of the sensing element 200.

Figure 3A:
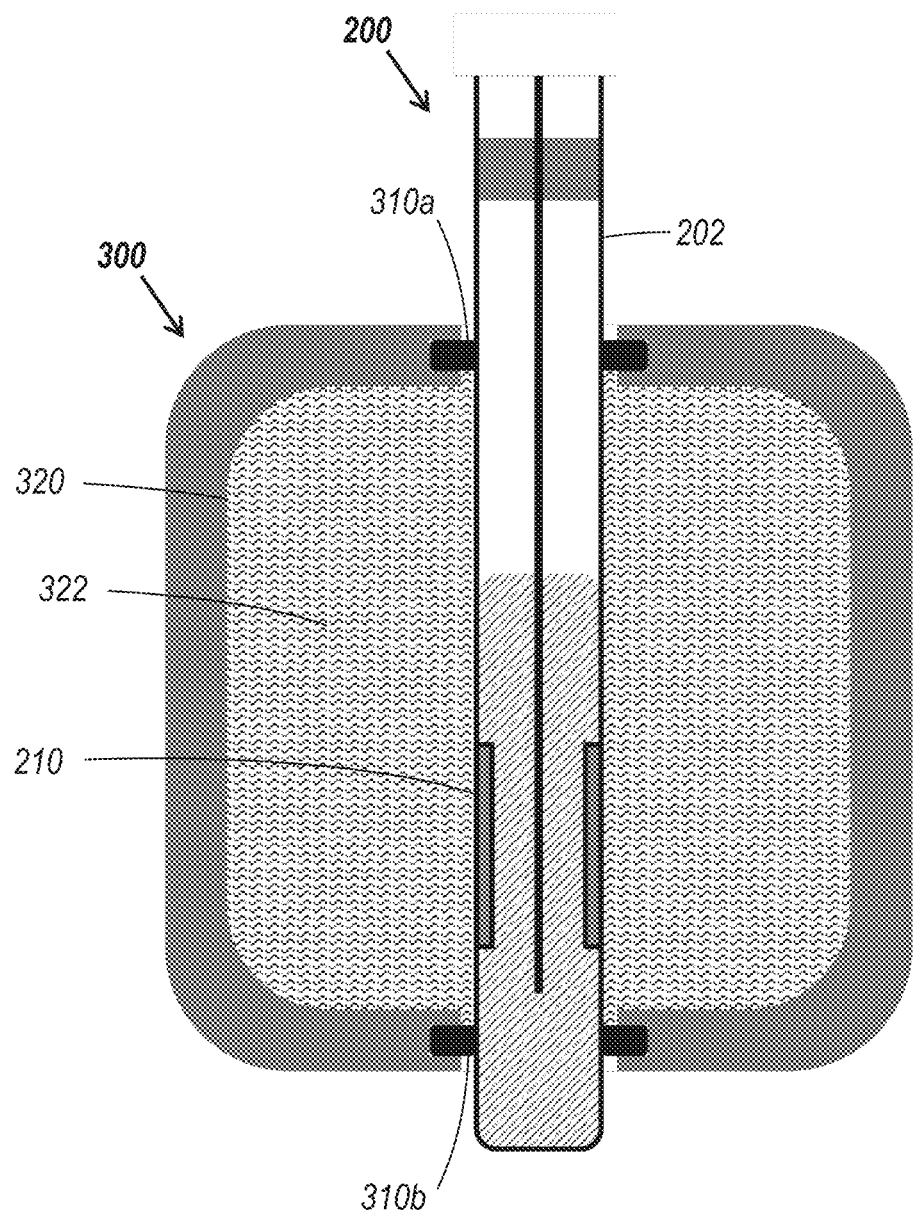
FIG. 3A is a side cross-sectional view schematically illustrating an embodiment of a sensor structure including a sensing element such as the sensing element of FIG. 2 and a storage compartment containing a calibration solution.

FIG. 3A is a side cross-sectional view schematically illustrating a sensor structure including a sensing element such as the sensing element of FIG. 2 and a storage compartment containing a calibration medium. In FIG. 3A, the sensing element 200 is positioned such that it extends through a storage compartment 300 having an internal storage chamber 320 filled with a material which serves as both a storage medium and a calibration medium 322. In some embodiments, the storage/calibration medium 322 may comprise a fluid, while in other embodiment, other forms of storage/calibration media may be used. For example, if the sensing element comprises a dissolved oxygen (DO) sensor, the storage/calibration medium may comprise a gas.

In particular, the sensing element 200 extends through both a proximal aperture of the storage compartment 300 having a proximal sealing element 310a positioned therein, and a distal aperture of the storage compartment 300 having a distal sealing element 310b positioned therein. The sensing element 200 extends along a longitudinal axis which passes through the centers of the proximal and distal apertures of the storage compartment 300.

In the position illustrated in FIG. 3A, the sensing element 200 of the probe is shown in a retracted position, in which the sensing surface 210 of the sensing element 200 is disposed within the storage compartment 300 and immersed in the storage/calibration medium 322. Because the sensing surface 210 is not located at the distal end 218 of the sensing element 200, the sensing element 200 includes an inactive distal portion 214 which can be exposed to a process medium or any other material without affecting the voltage (or other information) provided by the sensing element 200. In addition, because the inactive distal portion 214 does not include a sensing surface 210, the sensing element can be stored with part of the inactive distal portion 214 exposed, without affecting the sensing element 200 or requiring advance preparation before the sensing element 200 can be used in a measurement.

In particular, it can be seen in FIG. 3A that the inactive distal portion 214 interacts with the distal sealing element 310b to form part of the boundary encapsulating the storage/calibration medium 322 within the internal storage chamber 320 of the storage compartment 300. This is in contrast to the types of storage configurations required by the use of a sensing element such as the sensing element 100 of FIG. 1, having a sensing surface at the distal tip. If the sensing surface were at the distal end, storage of the sensing element with its distal end exposed would expose an active section of the sensing element to the exterior of the storage chamber, such that it would not be exposed to the storage medium. This could have a detrimental effect on the operation of the sensing element. In addition, more complex and mechanisms would be required to allow the sensing surface to be extended into the process medium to be tested, such as piercing a seal, or otherwise placing the interior of a storage chamber in fluid communication with the process medium. Such mechanisms would have irreversible effects on at least the composition of the fluid within the storage chamber, either by draining the storage chamber or allowing the storage medium to intermix with the process medium.

Figure 3B:
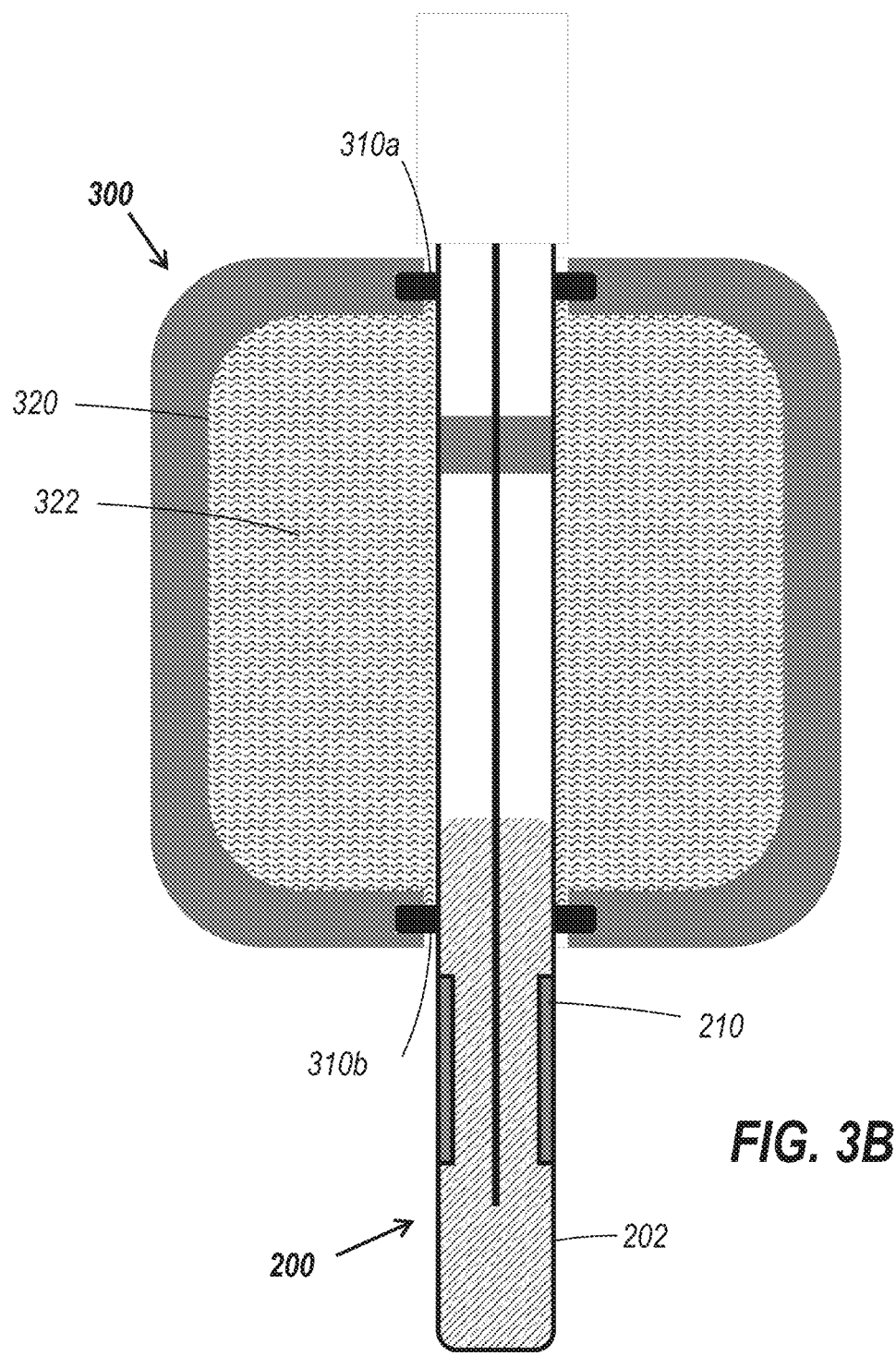
FIG. 3B is a side cross-sectional view schematically illustrating the sensor structure of FIG. 3A, with the sensing element displaced to expose the sensing structure.

In contrast, the configuration of FIG. 3A allows the sensing element 200 to be extended into the process medium, without placing the internal storage chamber 320 in fluid communication with the exterior of the storage compartment 300. FIG. 3B is a side cross-sectional view schematically illustrating the sensor structure of FIG. 3A, with the sensing element displaced to expose the sensing structure. In the position shown in FIG. 3B, the sensing element 200 has been longitudinally translated along the longitudinal axis of the sensing structure, such that the sensing surface 210 is now located outside of the sensing compartment 300. The proximal portion of the sensing element 200 now interacts with the distal sealing element 310b to form part of the boundary encapsulating the storage/calibration medium 322 within the internal storage chamber 320 of the storage compartment 300.

In some embodiments, the proximal and distal sealing elements 310a and 310b may be O-rings or any other suitable gasket or sealing element which maintains a substantially fluid tight seal even when the sealing element is being translated therethrough. The tolerance of the O-rings or other sealing element allows maintenance of the fluid seal even though the cross-sectional shape of the sensing element 200 may vary somewhat over the length of the sensing element 200.

During the translation of the sensing element 200 through the distal sealing element 310b, the seal is maintained, due to the outer cross-sectional area of the portion of the sensing element 200 in contact with the distal sealing element 310b being substantially constant, within the tolerance of the distal sealing element 310b. Even if some small amount of fluid is pulled out along with the exposed section of the sensing element 200, for example due to irregularities in the shape of the outer surface, the total volume of fluid exchange between the interior and the exterior of the storage compartment 300 may be minimal, and significantly less than embodiments in which the storage compartment is drained or completely exposed when the sensing element is extended. Thus, the volume of storage/calibration medium 322 pulled out of the storage compartment 300 may be less than substantially the entire volume of the storage compartment 300, in contrast to single use sensor designs in which the distal end of the sensing element is an active portion of the sensing element. In embodiments in which the interior of the storage compartment is exposed to the process medium, nearly all of the storage medium flows out of the storage compartment 300 due to draining or intermixing with the process medium, the volume of which can be substantially larger than the volume of the storage medium.

In contrast, through the use of media-retaining storage compartments as described herein, a greater amount of the storage/calibration medium can be retained after the sensor is extended (and retracted) into the storage medium. For example, more than 10% of the storage/calibration medium may be retained in the storage compartment, more than 30% of the storage/calibration medium may be retained in the storage compartment, more than 50% of the storage/calibration medium may be retained in the storage compartment, more than 70% of the storage/calibration medium may be retained in the storage compartment, more than 90% of the storage/calibration medium may be retained in the storage compartment, more than 95% of the storage/calibration medium may be retained in the storage compartment, more than 97% of the storage/calibration medium may be retained in the storage compartment, more than 98% of the storage/calibration medium may be retained in the storage compartment, or more than more than 99% of the storage/calibration medium may be retained in the storage compartment.

Figure 4A:
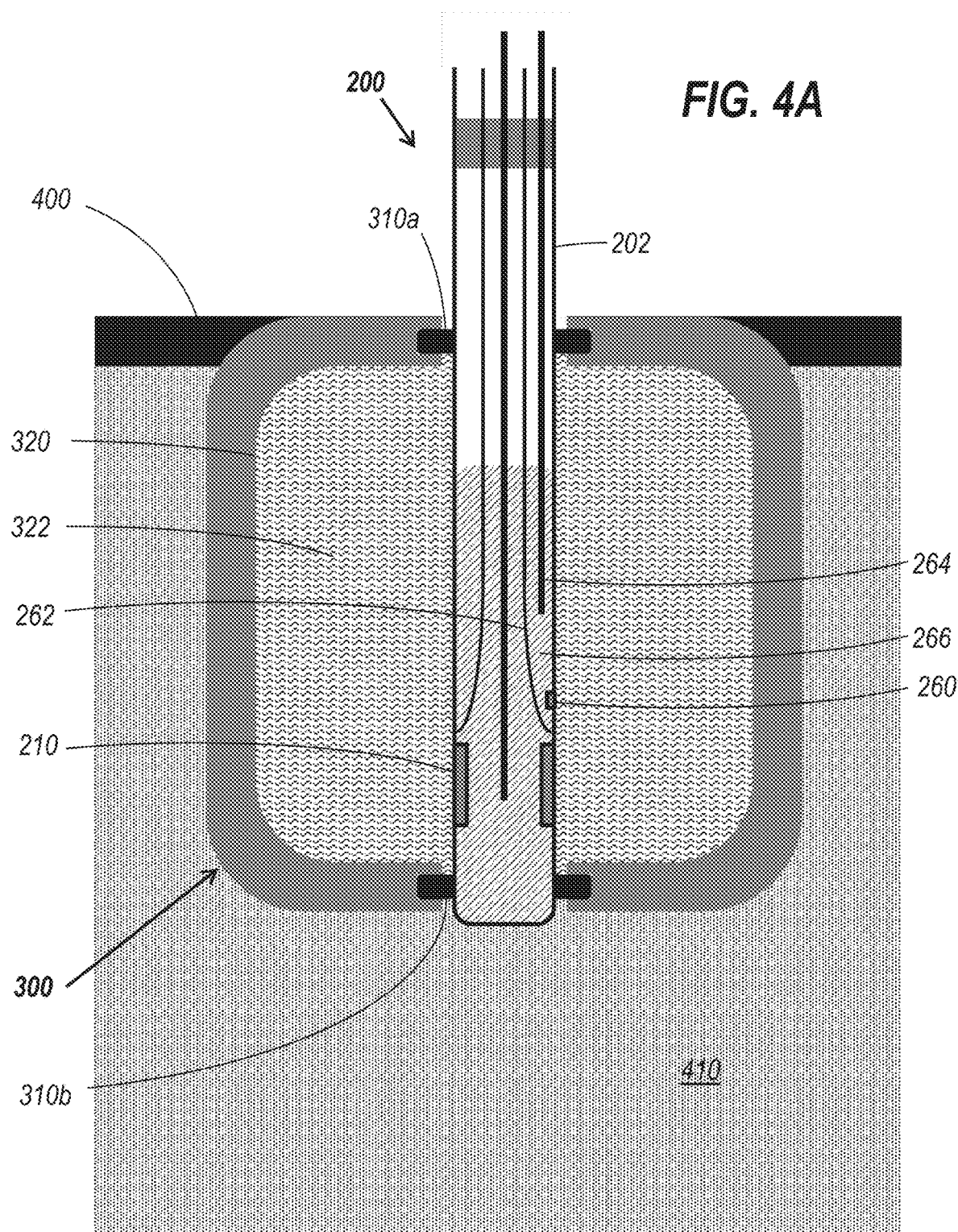
FIG. 4A is a side cross-sectional view schematically illustrating the sensor structure of FIG. 3A, shown in a sealed position relative to media to be tested.

The sensor structure of FIG. 3A can be integrated into or otherwise installed in a bioreactor such as a flexible single-use bioreactor bag. FIG. 4A is a side cross-sectional view schematically illustrating the sensor structure of FIG. 3A, shown in a sealed position relative to media to be tested. It can be seen that the proximal side of the storage compartment 300 is attached to, integrated with, or otherwise secured relative to the flexible wall 400 of the bioreactor, such that the storage compartment 300 is located on the interior of the bioreactor, and extends into the process medium 410. In other embodiments, however, the storage compartment 300 may be located at least partially outside of the wall 400 of the bioreactor, or entirely outside the wall of the bioreactor, and a wide variety of suitable configurations may be used.

When the sensing element is in the retracted position of FIG. 4A, the distal sealing element 310b maintains a fluid-tight seal between the storage/calibration medium 322 and the process medium 410. The composition of the storage/calibration medium 322 remains constant and the pH remains at a known, constant value. At some point prior to extension of the sensing element 420 into the process medium 410, a validation or calibration process may be performed by measuring the voltage from the sensing element 200 to confirm that it is consistent with the expected reading, based on the known pH of the storage/calibration medium 322.

It can also be seen in FIG. 4A that the sensing element 200 includes an integrated reference electrode as part of the single structure. The sensing element 200 includes an internal wall separating a first internal region of the body 202 from a second internal region. The first internal region includes the half-cell element lead 204 and a volume of internal electrolyte 206 in fluid communication with the sensing surface 210, while the second internal region includes a half-cell element lead 264 and a second volume of internal electrolyte 266 in fluid communication with a liquid junction 260. When in the position shown in FIG. 4A, both the sensing surface 210 and the liquid junction 260 are in contact with the storage/calibration medium 322.

Figure 4B:
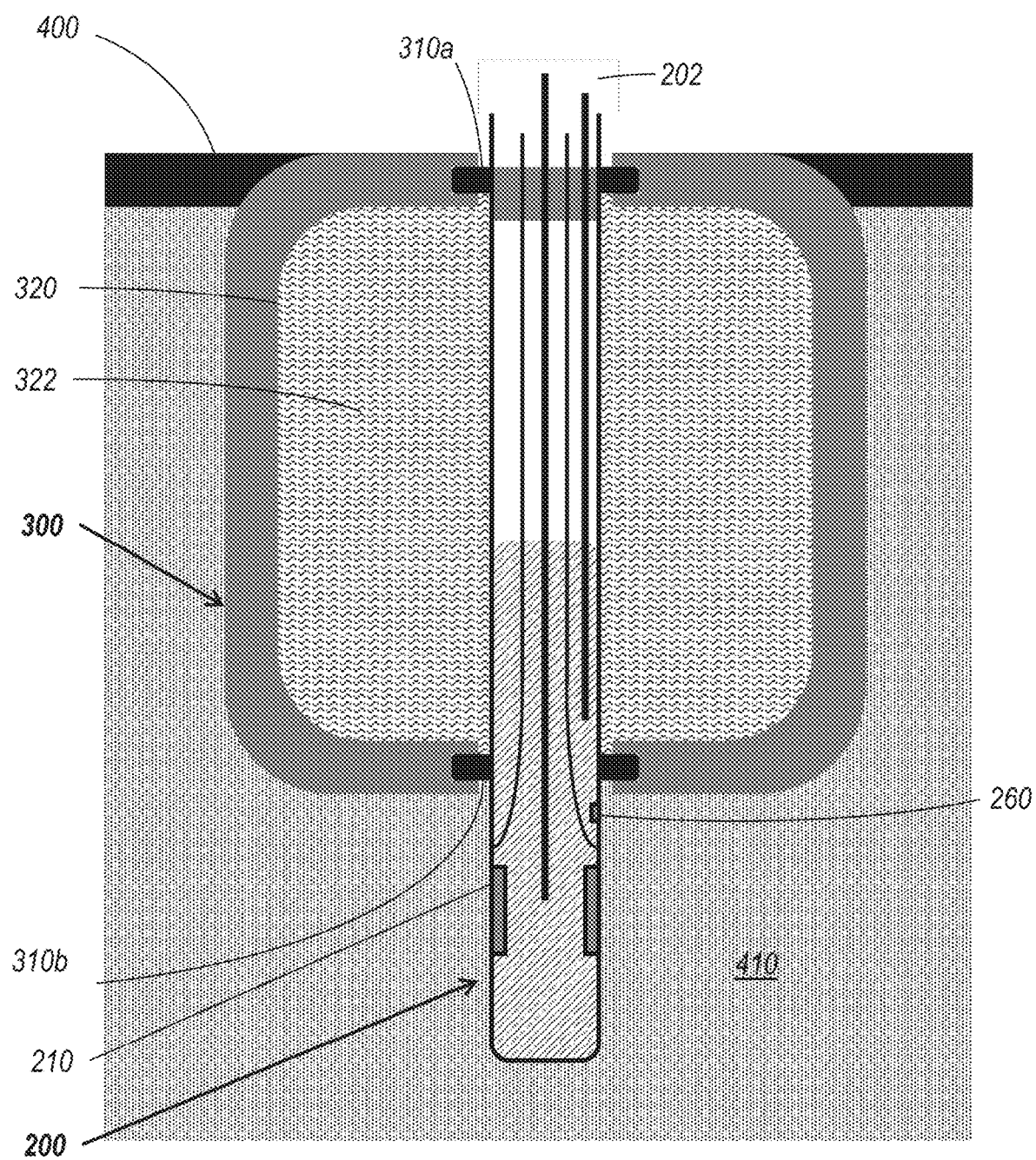
FIG. 4B is a side cross-sectional view of the sensor structure in FIG. 4A, shown in an extended position in which the sensing structure of the sensing element is exposed to the media to be tested.

The sensing element 200 may be moved in the longitudinal direction to the position shown in FIG. 4B. During this process, the distal sealing element 310b maintains a fluid seal with the constant-diameter section of the sensing element 200, preventing or minimizing fluid exchange between the storage/calibration medium 322 and the process medium 410. When in the position shown in FIG. 4B, both the sensing surface 210 and the liquid junction 260 are in contact with the process medium 410, as the length of travel is sufficient that both the sensing surface 210 and the liquid junction 260 pass through the sealing element. To maintain the fluid-tight seal, the section of substantially constant cross-sectional area includes the section of the sensing element 200 which includes both the sensing surface 210 and the liquid junction 260. When in the extended position, the pH of the process medium 410 may be measured by measuring the voltage from the sensing element 200, when the sensing surface 210 and the liquid junction 260 are immersed in the process medium 410.

Once the pH of the process medium 410 is measured, the sensing element 200 can then be retracted into the storage compartment 300. The distal sealing element 310b again operates to prevent or minimize fluid exchange between the storage/calibration medium 322 and the process medium 410 by maintaining a fluid-tight seal during the retraction. The shape and configuration of the sensing element 200 allow the storage/calibration medium 322 to be retained within the storage compartment 300 even after the extension and retraction of the sensing element 200. In contrast to other designs in which the storage medium is not retained, or mixes with the process medium, the sensing surface 210 of the sensing element 210 is retained within a storage/calibration medium 322 of known composition and pH, due to the lack of significant mixing of the storage/calibration medium 322 with the process medium 410. This enables a post-measurement calibration or validation process, in which the voltage from the sensing element 200 is measured to confirm that it is consistent with an expected reading, based on the known pH of the storage/calibration medium 322, to confirm that the probe is operating correctly. This can be done in a non-destructive fashion, without cutting into the flexible wall 400 or otherwise removing the sensing element 200 from the bioreactor.

By inhibiting fluid flow between the storage/calibration medium 322 and the process medium 410, a wider range of possible compositions of the storage/calibration medium 322 may be possible. If a storage compartment is designed such that all of the storage medium contained therein will be mixed with the process medium, the composition of the storage medium may be chosen so that it will have a pH near 7.0 at room temperature, so as to have a minimal effect on the pH or composition of the process medium. If, however, the storage/calibration medium 322 can be retained within the storage compartment, with minimal if any mixing with the process medium, storage/calibration media with a wider range of possible compositions and pH may be used. For example, in one embodiment, a storage/calibration medium 322 with a pH of roughly 4.0 at room temperature may be used. By providing a larger difference between the pH of the storage/calibration medium 322 and the expected pH of the process medium 410, an error in the operation of the sensing element will be more apparent, as the measured voltage will differ from the expected voltage by a larger amount.

In other embodiments, storage/calibration media having a pH of 4.01, 6.86, 9.18, or 10.05 at room temperature may be used. However, a wide variety of other pH ranges may also be suitable as storage/calibration media. In some embodiments, the pH at room temperature may be between 0 and 14, between 1 and 13, between 3 and 12, between 4 and 10.5, between 5 and 10.5, or between 6 and 10.5. In some embodiments, the pH at room temperature may be less than 6.5, less than 6.0, less than 5.0, or less than 4.0.

In embodiments in which the sensing structure comprises a type of sensor other than a pH sensor, the calibration medium may be chosen based on the property to be measured by the sensor. As discussed above, the calibration medium may comprise a gas or other material.

Even in the case of a smart sensor, in which the calibration can be performed prior to sterilization and subsequent installation into a flexible bioreactor bag, and the calibration data stored in a memory circuit of the smart sensor, the use of the storage medium as a calibration medium can still provide a verification of the continued functionality of the smart sensor, as a measurement sufficiently different from the known pH of the storage medium can provide an indication that the sensor has failed or is otherwise not providing an accurate measurement of the pH to which the sensing surface is exposed. Because this storage solution is maintained in substantially its original state, with minimal if any exposure to the process medium, this verification or failure check can also be performed after the sensing element is retracted back into the storage chamber. If the pH measurement of the process medium is different from an expected measurement, the retraction and subsequent measurement of the sensing element of the probe when exposed to the storage solution can provide a rapid and non-destructive check or verification of the operation of the measurement probe while the process is still ongoing. Because the calibration medium is retained in the storage compartment, the sensing element can be moved to a medium with known pH without the need to compromise the sterility of the ongoing process by physically removing the engaged probe structure from the flexible bioreactor and compromising the sterility of the process medium.

Figure 5A:
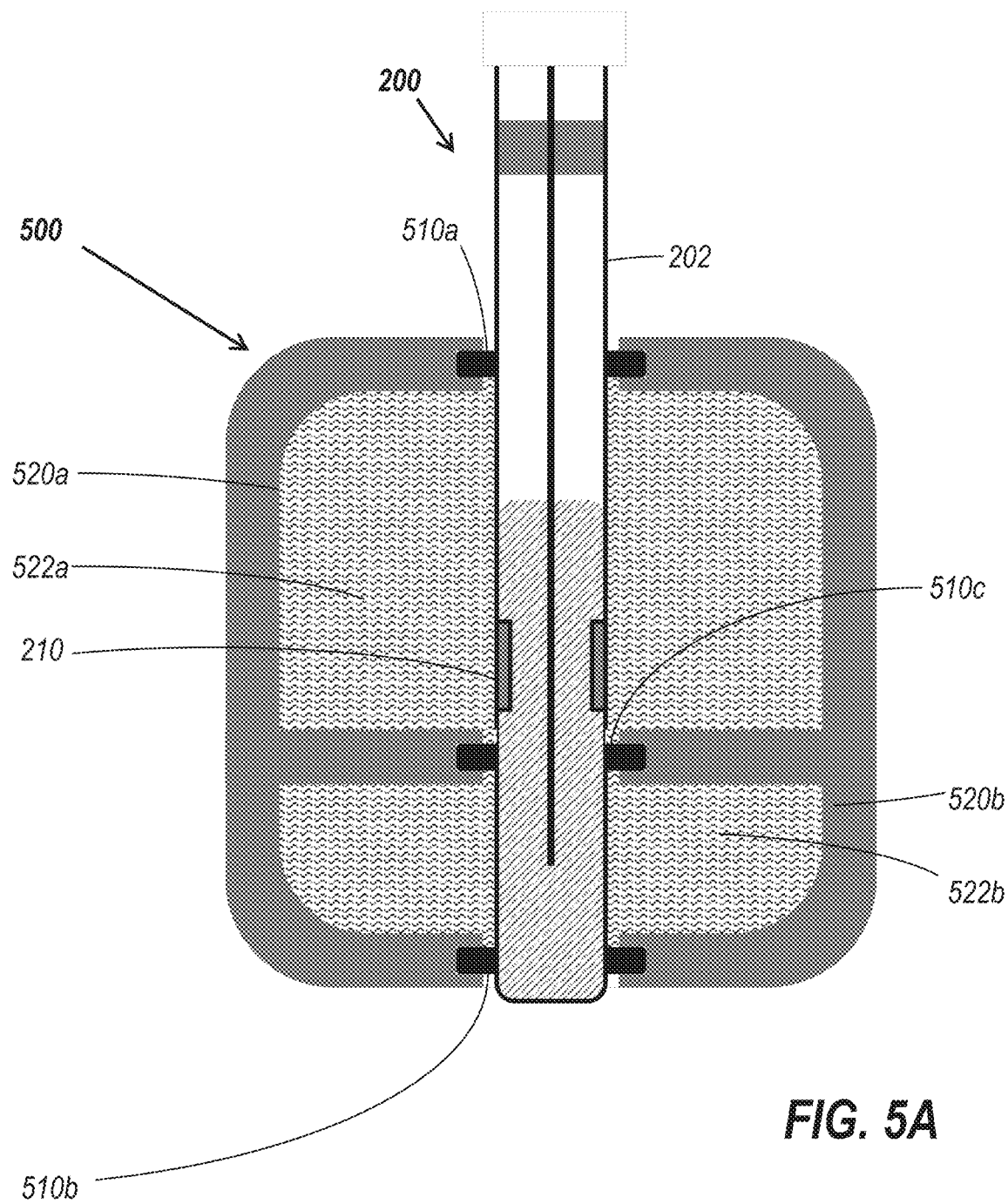
FIG. 5A is a side cross-sectional view schematically illustrating an embodiment of a sensor structure including a dual-chamber storage/calibration compartment, with the sensing structure of the sensing element located in the upper chamber.

In some embodiments, the shape of the sensing element can be used in conjunction with a dual-chambered storage compartment to provide two-point on-site calibration of a sensor, or two-point verification. FIG. 5A is a side cross-sectional view schematically illustrating a sensor structure including a dual-chamber storage/calibration compartment, with the sensing structure of the sensing element located in the upper chamber. The storage compartment 500 is similar to the storage compartment 300 of FIG. 3A, but differs in that it includes an internal wall separating a distal chamber 520b from a proximal chamber 520a. The sensing element 200 cooperates with an internal sealing element 510c to maintain a seal between the proximal and distal chambers 520a and 520b. Because this internal seal will be maintained during translation of the sensing element 200 through the storage compartment 500, with minimal fluid flow between the chambers, the proximal chamber 520b may retain a storage/calibration medium 522a different from the storage/calibration medium 522b in the distal chamber 520b. In some embodiments, one of the chambers may include a medium which functions only as a calibration medium, with the sensing surface 210 of the sensing element being stored in the other of the two chambers for extended periods of time.

When the pH of the storage/calibration medium 522a differs from the pH storage calibration medium 522b, a two-point validation or calibration process may be performed prior to and/or after measurement of a process medium. The voltage of the sensing element 200 may be measured when the sensing surface 210 is immersed in the storage/calibration medium 522a.

Figure 5B:
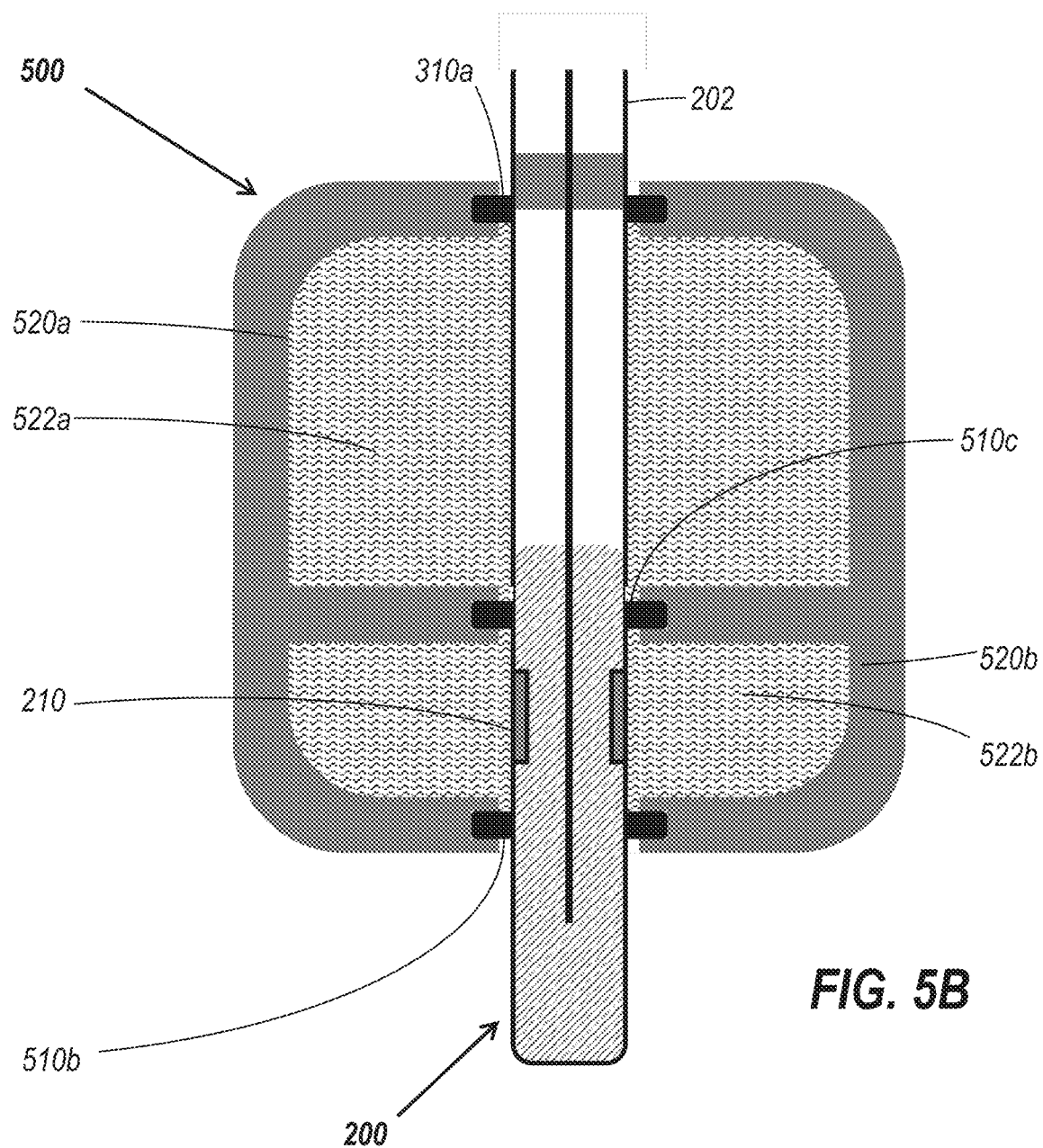
FIG. 5B is a side cross-sectional view of the sensor structure of FIG. 5A, with the sensing structure of the sensing element located in the lower chamber.

The sensing element 210 may then be translated in the distal direction. FIG. 5B is a side cross-sectional view of the sensor structure of FIG. 5A, with the sensing structure of the sensing element located in the lower chamber. The voltage of the sensing element 200 may also be measured when the sensing surface 210 is immersed in the storage/calibration medium 522b. The measured voltage when the sensing surface 210 is exposed to the storage/calibration media 522a and 522b can be compared with the expected voltages at the known pH values of the storage/calibration media 522a and 522b, and used to verify or calibrate the sensing element 200.

Figure 5C:
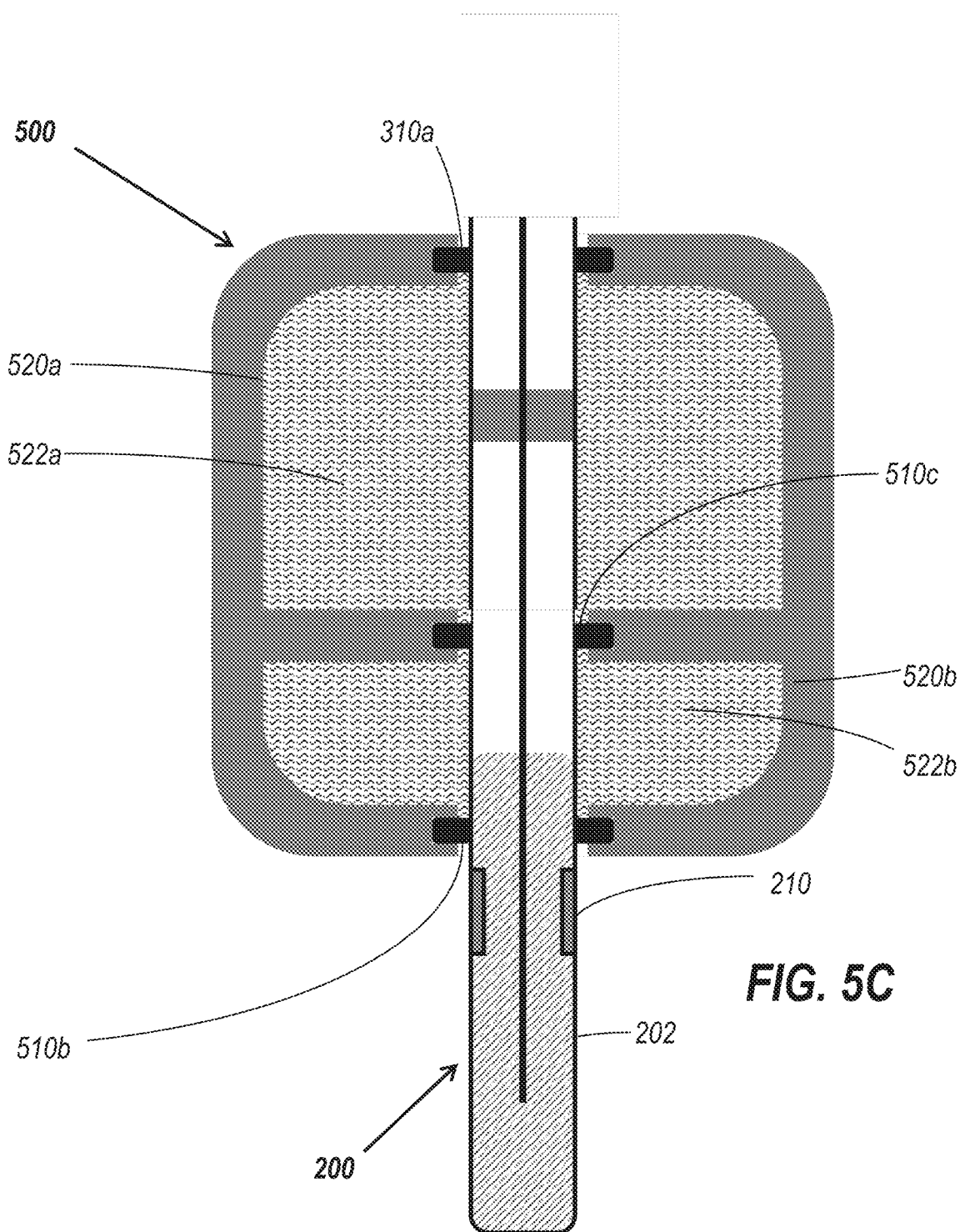
FIG. 5C is a side cross-sectional view of the sensor structure of FIG. 5A, with the sensing structure of the sensing element exposed to the exterior of the storage/calibration compartment.

Once done, the sensing element 200 may then be extended into a process medium for testing and used for measurement and control of the process. FIG. 5C is a side cross-sectional view of the sensor structure of FIG. 5A, with the sensing structure of the sensing element exposed to the exterior of the storage/calibration compartment. After measurement of the process medium, the sensing element may then be retracted through both chambers 520a and 520b, and measurements may be taken in each chamber as part of a post-measurement validation process.

Figure 6:
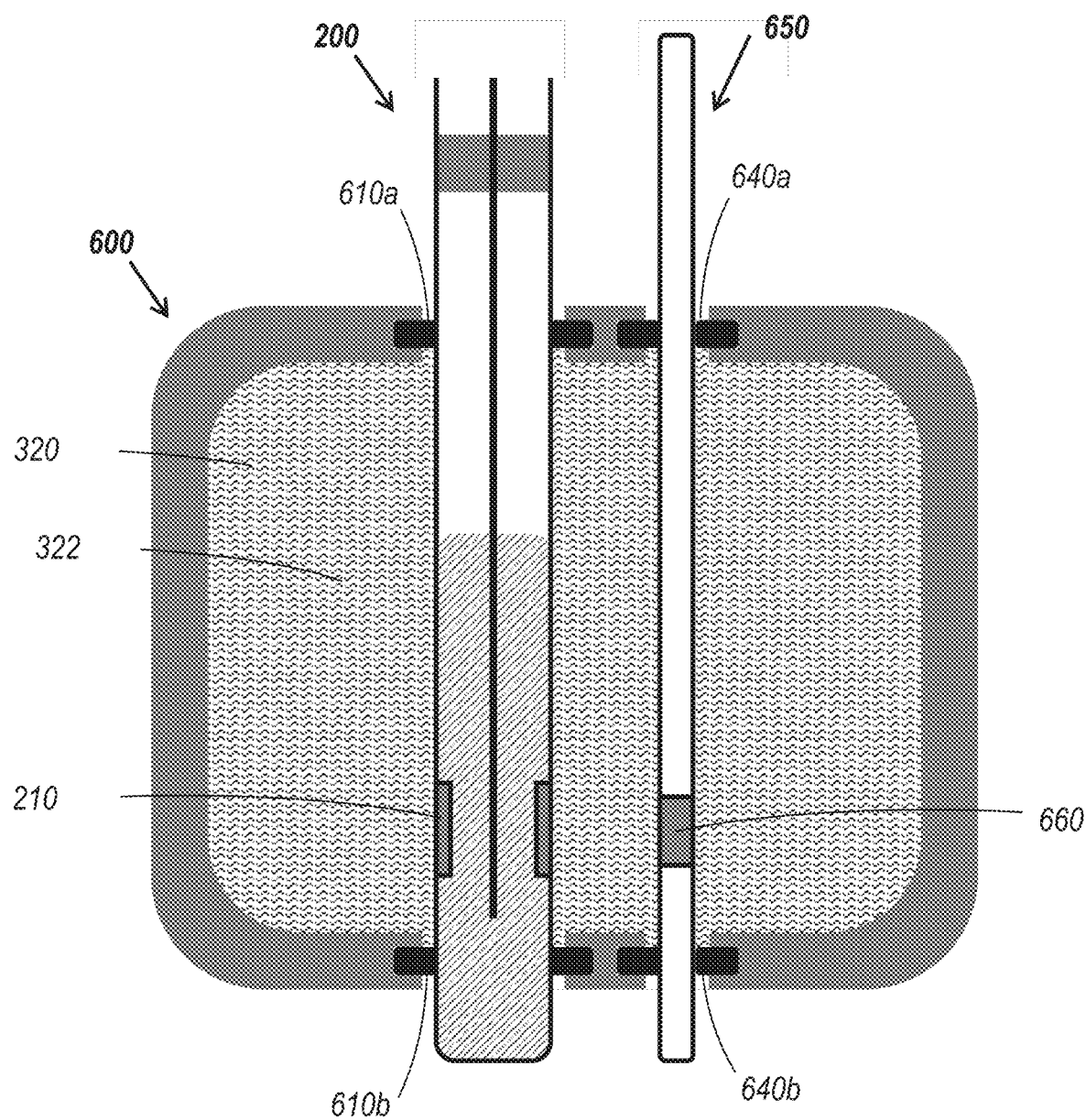
FIG. 6 is a side cross-sectional view schematically illustrating an embodiment of a storage compartment configured to retain therein a pair of sensing elements oriented parallel to one another.

As discussed elsewhere herein, the sensing structure may also include additional components not specifically illustrated in the figures, such as a reference electrode. FIG. 6 is a side cross-sectional view schematically illustrating a storage compartment configured to retain therein a pair of sensing elements oriented parallel to one another. The storage compartment 600 differs from the storage compartment 300 of FIG. 3A in that the storage compartment 600 includes a pair of proximal sealing elements 610a and 640a and a pair of distal sealing elements 610b and 640b. The sealing elements 610a and 610b are dimensioned and spaced to receive the sensing element 200, while the sealing elements 610b and 610b are dimensioned and spaced to receive a separate sensing element 650, which may serve as the reference electrode for a probe.

The reference half-cell element 650 includes a liquid junction 660, and can be configured to move along with the sensing element 200 such that when the sensing surface 210 is exposed to the storage/calibration medium 322, the liquid junction 660 is as well. Similarly, when the sensing surface 210 is exposed to a process medium 322, the liquid junction 660 will also be exposed to the process medium. A section of substantially constant cross-sectional area extending to either side of the sensing surface 600 allows the sealing element 610b to maintain a fluid-tight seal during translation of the reference half-cell element 650 therethrough.

Although the embodiments described herein are primarily described in the context of pH sensors in conjunction with bioreactors, the features described herein can be utilized in conjunction with other types of sensors, and in other contexts. For example, in addition to use with bioreactor bags, or tubing or other conduits in fluid communication with bioreactor bags, the sensing elements and associated components may be used with or integrated into a wide variety of other elements in a process flow. These elements may be flexible bags or other containers used in media preparation, upstream of a cell culture, as well as in various purification steps downstream of a cell culture. Similarly, embodiments may be used in any other suitable application, in conjunction with any suitable type of sensor. For example, the storage compartment and sensing element geometry can be used to facilitate on-site calibration during, for example, field testing of pH or other measurements, with the ability to retract the measurement probe into a storage compartment that protects the probe and allows for calibration or verification of the probe operation before or after tests.

Figure 7:
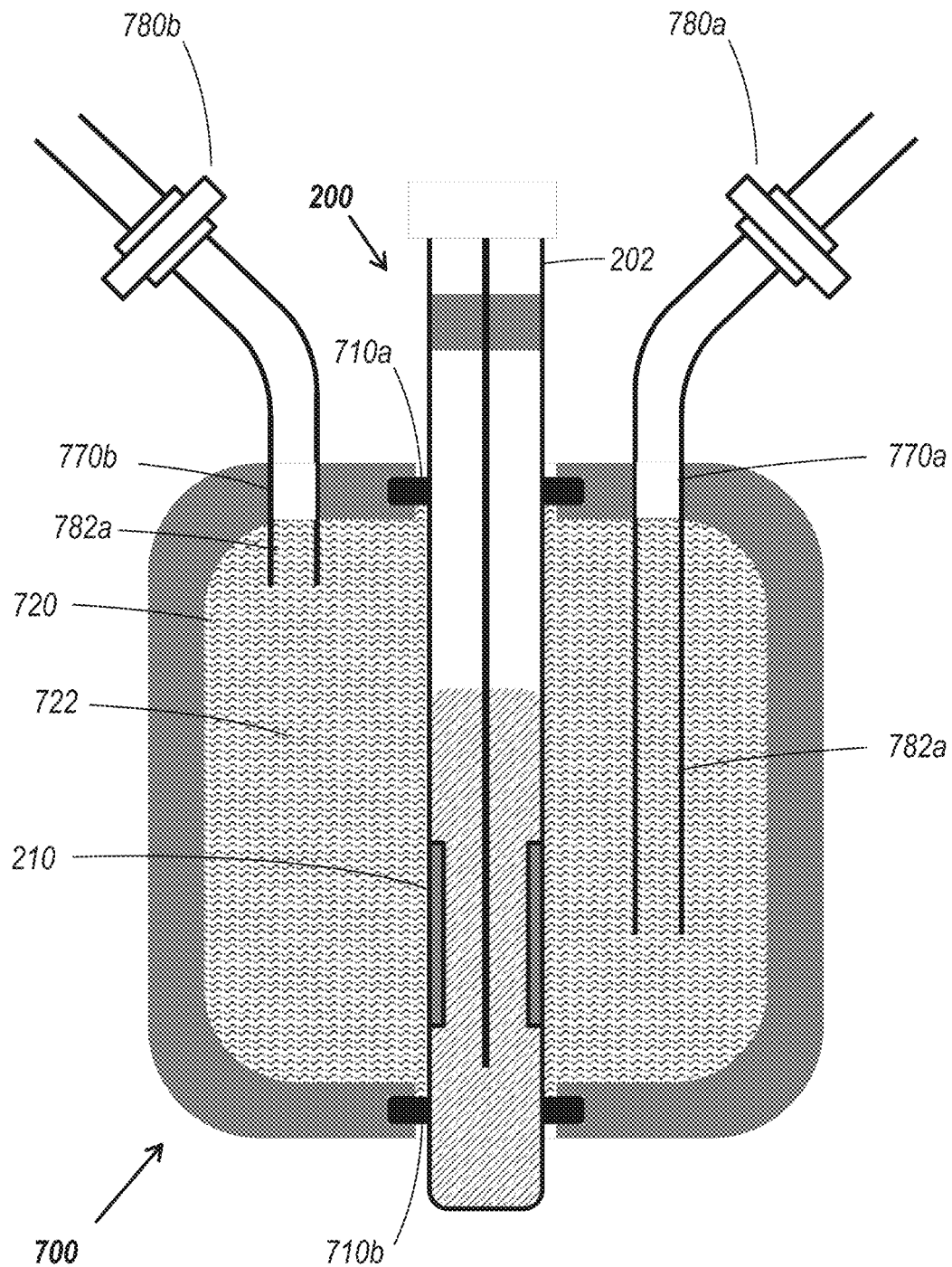
FIG. 7 is a side cross-sectional view schematically illustrating an embodiment of a sensor structure including a sensing element such as the sensing element of FIG. 2 and a storage compartment including two ports allowing access to the storage medium inside the storage compartment.

In some embodiments, a storage compartment can include port or other opening to replace, alter, or otherwise interact with the storage/calibration medium. FIG. 7 is a side cross-sectional view schematically illustrating a sensor structure including a sensing element such as the sensing element of FIG. 2 and a storage compartment including two ports allowing access to the storage medium inside the storage compartment. The storage compartment 700 includes a first port 780a, which may serve as an inlet port, extending through an aperture 770a in the wall of the storage compartment 700, and a second port 780b, which may serve as an outlet port, extending through an aperture 770b in the wall of the storage compartment 700. The ports 780a and 780b may include filters, which may in some embodiments be submicron filters. The ports 780a and 780b allow access to the storage/calibration medium 722 within the storage compartment 700 without compromising the sterility of the storage compartment 700. This can be used to replace, refill, or otherwise alter the volume or composition of the storage/calibration medium 722 within the storage compartment 700.

In certain embodiments discussed herein, the operation of a sensing element in conjunction with a media-preserving storage and calibration chamber is discussed in the context of extending the sensing element into a flexible bioreactor bag or similar process container to access the process medium. In other embodiments, however, the sensing element may be used in conjunction with a tube or other component which is in fluid communication with the process container, or can be selectively placed in fluid communication with the process container. In some embodiments, the sensing element can be extended into a cavity through which process medium or other medium to be tested is flowing.

Figure 8:
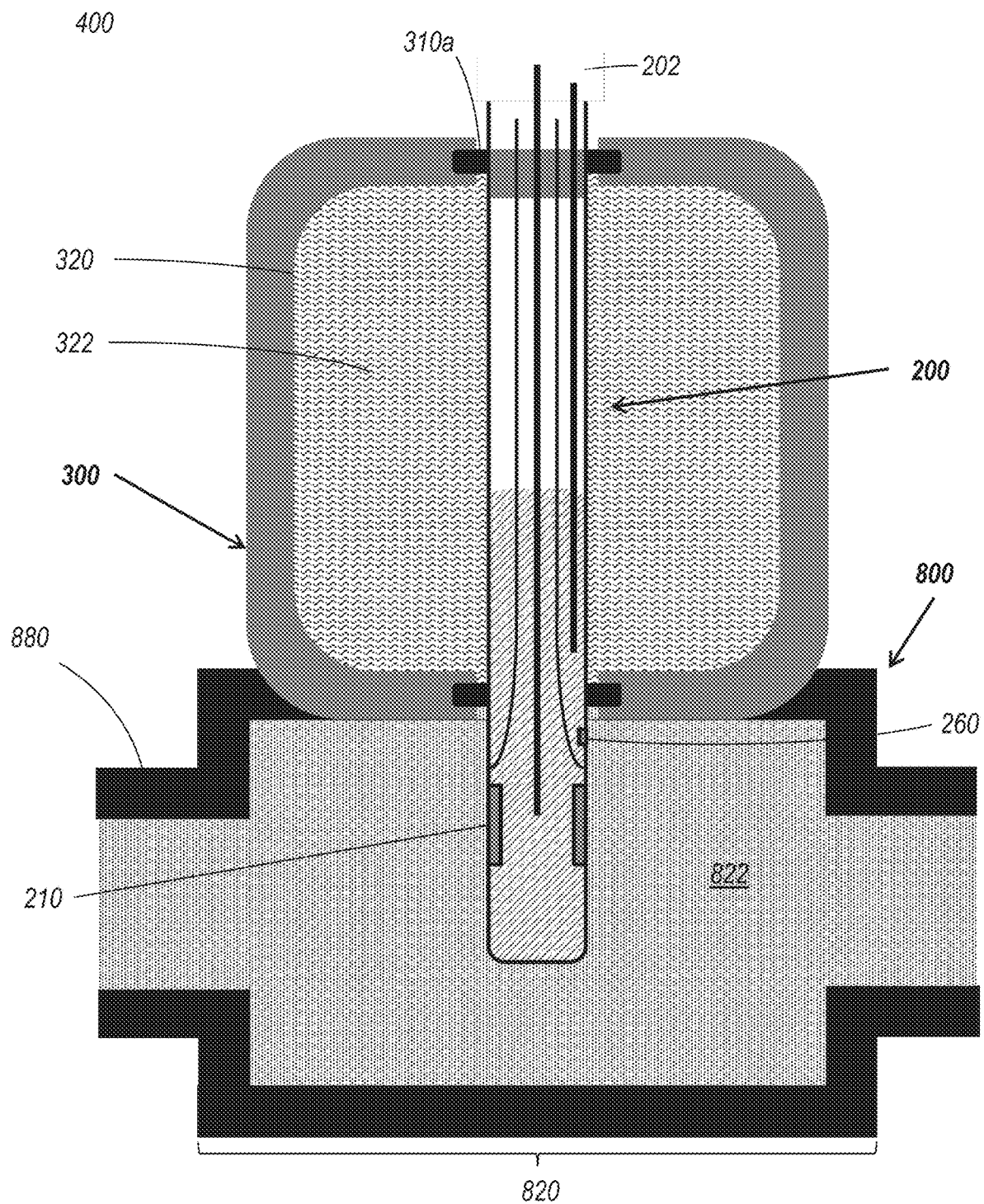
FIG. 8 is a side cross-sectional view schematically illustrating an embodiment of a sensor structure including a sensing element such as the sensing element of FIG. 2 and a storage compartment, where the storage compartment is disposed adjacent a portion of a fluid path.

FIG. 8 is a side cross-sectional view schematically illustrating a sensor structure including a sensing element such as the sensing element of FIG. 2 and a storage compartment, where the storage compartment is disposed adjacent a portion of a fluid path. In FIG. 8, the storage compartment 300 is located adjacent a fluid or gas conduit 800, such that the sensing element 200 can extend into the conduit 800 and expose the sensing surface 210 (and liquid junction 260, if integrated within the sensing element 200) into the medium 822 within the conduit 800. In some embodiments, the medium 822 may be flowing through the conduit 800 during at least part of this process.

In the illustrated embodiment, the conduit 800 includes a section 820 having a larger cross-sectional area than adjacent sections 880 of the conduit 800. Such a configuration can be used when the cross-sectional area of the conduit 800 is small enough relative to the size of the exposed portion of the sensing element 200 that the sensing element 200 could not extend a sufficient distance into the conduit 800 to expose the sensing surface 210 and liquid junction 260, or would significantly occlude the flow of the medium 822 through the conduit 800. In embodiments in which the medium 822 is flowing through the conduit 800, the sensing element 200 may remain in an extended position to measure a property of the medium 822 at multiple points in time. Multiple measurements over a period of time may also be made in any of the embodiments discussed herein, such as to measure the progress of a process over time.

In other embodiments, the sensing element need not be cylindrical, but may be any suitable shape. FIG. 9A is a perspective view schematically illustrating another embodiment of a sensing element. FIG. 9B is a side view schematically illustrating the sensing element of FIG. 9A. The sensing element 900 includes a planar side 902, and a sensing surface 910 located on or in the planar side 902. In the illustrated embodiment, the sensing element 900 is in the shape of a rectangular prism, but in other embodiments, any other suitable shape may be used. The side having the sensing surface 910 need not be planar, but may be any suitable shape, as described in greater detail below. The sensing element 900 may also include a half-cell element lead and an internal electrolyte, as discussed elsewhere herein, and may also include an integrated reference electrode, which may include a liquid junction adjacent the sensing surface 910.

Figures 10A, 10B:
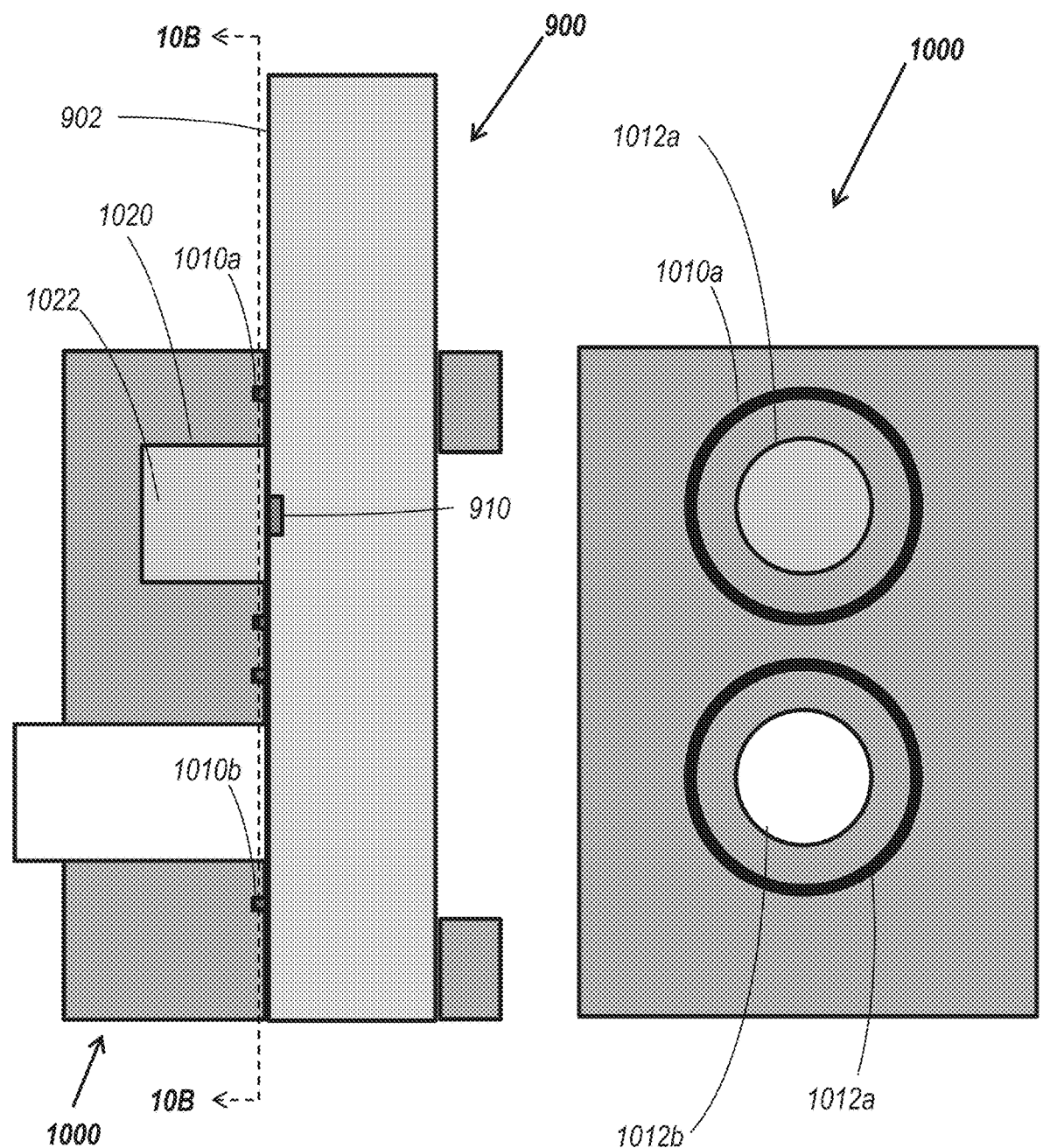
FIG. 10A is a side view schematically illustrating an embodiment of a sensor structure including the sensing element of FIG. 9A, shown in a position in which the sensing surface is exposed to a storage/calibration medium.
FIG. 10B is a cross-sectional view of the sensor structure of FIG. 10A, taken along the line 10B-10B of FIG. 10A.

FIG. 10A is a side cross-sectional view schematically illustrating a sensor structure including the sensing element of FIG. 9A, shown in a position in which the sensing structure is exposed to a storage/calibration medium. FIG. 10B is a cross-sectional view of the sensor structure of FIG. 10A, taken along the line 10B-10B of FIG. 10A. The sensor structure 1000 includes a pair of apertures 1012a and 1012b, surrounded by sealing elements 1010a and 1010b, respectively. The sealing elements may comprise O-rings or other gaskets, or any other suitable sealing structure. One aperture is in fluid communication with a storage compartment 1020 containing a storage medium 1022, which may also serve as a calibration medium. The other aperture is in fluid communication with an area which may be filled with or otherwise exposed to a process medium to be tested. The planar side 902 of the sensing element cooperates with the sealing element 1010a to retain the storage/calibration medium 1022 within the storage compartment 1020. In the position shown in FIG. 10A, the sensing surface 910 of the sensing element 900 is exposed to the storage/calibration medium in the storage compartment 1020.

Figure 10C:
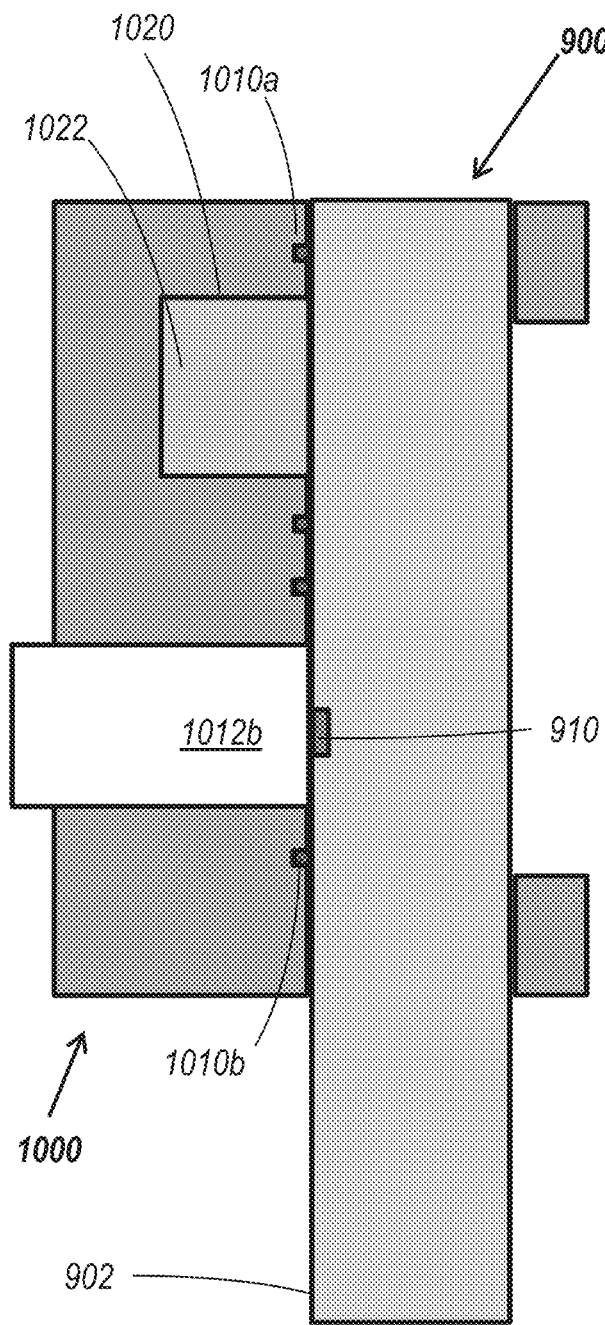
FIG. 10C is a side view of the sensor structure of FIG. 10A, with the sensing element moved to a position in which the sensing surface can be exposed to a process medium.

FIG. 10C is a side view of the sensor structure of FIG. 10A, with the sensing element moved to a position in which the sensing surface can be exposed to a process medium. The sensing element 900 is translated in a direction parallel to the planar side 902, such that the planar side 902 slides along the sealing elements 1010a and 1010b until the sensing surface 910 is aligned with the aperture 1012b, allowing exposure of the sensing surface 910 to a process medium to be tested.

Figure 11B:
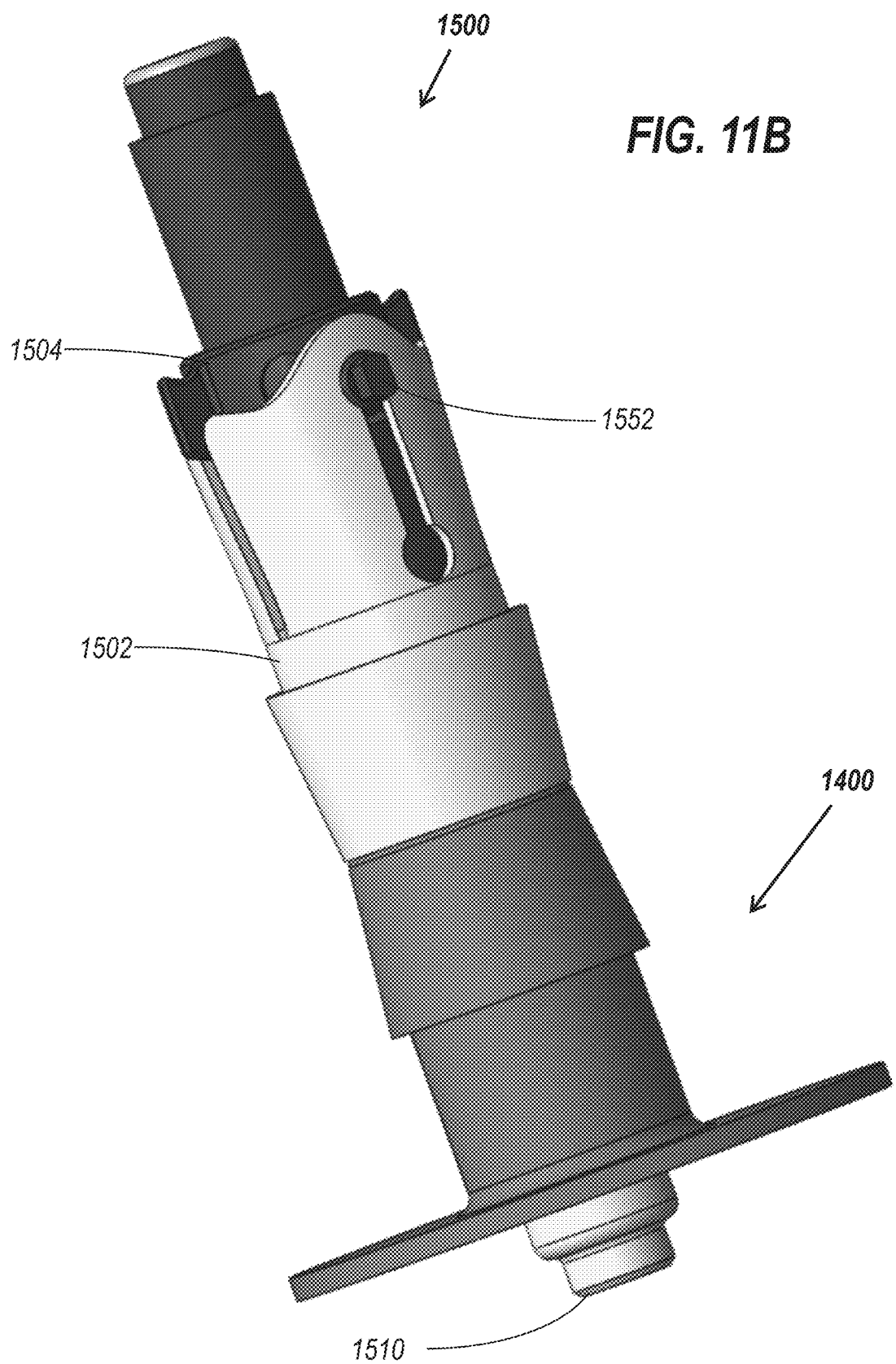
FIG. 11B is a perspective view of the sensor structure of FIG. 11A.

FIG. 11A is a side view of another embodiment of a sensor structure including a sensing element such as the sensing element of FIG. 2 and a storage compartment containing a storage solution, shown inserted into a tube port. FIG. 11B is a perspective view of the sensor structure of FIG. 11A.

The sensor structure 1500 may be a single-use sensor such as a single-use pH sensor, and includes a sensor housing 1502 which includes a storage compartment 1540 containing a storage solution 1542. The sensor housing 1502 can be secured relative to a tube port 1400 as shown, or other suitable structure. The sensor structure 1500 also includes a movable component 1504 which is longitudinally translatable relative to the sensor housing 1502, and which supports a sensing element 1520 such as the sensing element 200 of FIG. 2.

A sealing element such as an external gasket 1528 or O-ring cooperates with the internal surface of the tube port 1400 to maintain the integrity of the bioreactor bag in which the tube port 1400 is installed. To illustrate the fit of sensor structure 1500 within tube port 1400, FIG. 11A shows the tube port 1400 in partial cutaway view, whereas FIG. 11B shows the external surface of the tube port 1500. The external gasket 1528 is located between the sensor housing 1502 and the tube port 1400, and does not extend through the interior of the storage compartment 1540 or contact the storage solution 1542 inside. A connector 1580 extending from the proximal end of the sensor structure 1500 allows connections to be made with an external instrument or system.

Translation of the movable component 1504 of the sensor structure 1500 allows the sensing element 1520 to be translated moved from a first position in which the sensing surface 1522 of the sensing element 1520 is retained within the storage compartment 1540 and exposed to the storage solution 1542. The sensing element 1520 can be moved to a second position in which the sensing surface 1522 has been translated through the distal internal gasket near the distal tip 1510 of the sensor housing 1502, allowing exposure of the sensing surface 1522 to a process medium.

Control over the longitudinal translation of the movable component 1504 and the sensing element 1520 with respect to the sensor housing 1502 can be provided through the use of an outwardly extending bolt 1552 or other feature which is retained within a longitudinally-extending aperture 1590 in the sensor housing 1502. In the illustrated embodiment, the aperture 1590 includes a distal wider region 1592a and a proximal wider region 1592b connected to one another by a narrower longitudinal channel 1594. The aperture 1590 can be dimensioned, in conjunction with other components and features of the sensor structure 1500, to define or constrain the manner in which the movable component 1504 can be moved relative to the sensor housing 1502.

In one embodiment, the bolt 1552 may have a shape which varies over the height of the bolt, and may be resiliently supported by a cantilevered portion of the movable component. In particular, an upper section of the bolt 1552 may have a narrower section, allowing it to be translatable along the narrower longitudinal channel 1594 when the bolt 1552 is pressed inwards. When the bolt is no longer pressed inwards, it will flex back outwards, and the thicker lower section of the bolt 1552 will retain the bolt in place within one of the wider regions 1592a or 1592b. Outwardly extending grips or wings 1554 can assist with translation of the movable component of the sensor 1500 relative to the housing, and may be movable through longitudinal channels in the sensor housing 1502.

Other configurations are possible, as well. In another embodiment, the bolt 1552 or similar structure may include a rotatable section, such that the bolt must be rotated to a particular position to be translatable along the narrower longitudinal channel 1594, and can then be rotated back once in place in one of the wider regions 1592a or 1592b to retain the movable component of the sensor 1500 relative to the sensor housing 1502.

Figure 11C:
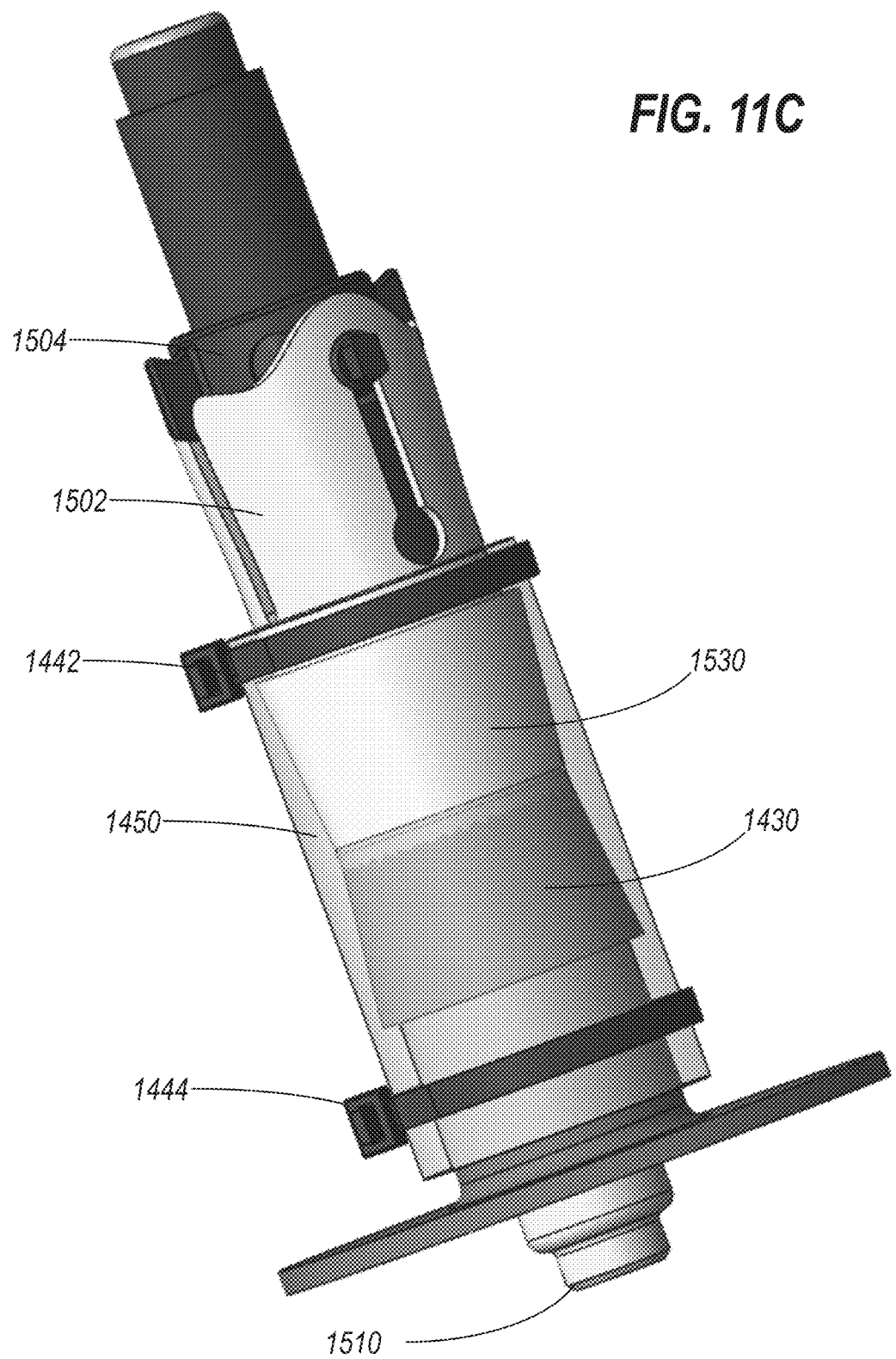
FIG. 11C is a perspective view of an embodiment in which a supplemental securement device is used to secure the sensor structure of FIG. 11A relative to the tube port.

FIG. 11C is a perspective view of an embodiment in which a supplemental securement device is used to secure the single-use sensor relative to the tube port. It can be seen in FIG. 11C that a length of tubing 1450 extends over the point at which the proximal end of the tube port abuts a facing surface of the sensor housing 1502. A first compressive member 1442 is located proximal the flared proximal portion 1530 of the sensor housing 1502 and a second compressive member 1444 is located distal the flared portion 1430 of the tube port 1400 which abuts the flared portion 1530 of the sensor housing 1502. In some embodiments, the compressive members 1442 and 1444 comprise zip ties, bands, or similar structures.

The compressive members 1442 and 1444 crimp the outer edges of the tubing 1450 and cooperate with the flared sections of the collar portions 1430 and 1530 to prevent the single use sensor 1500 from being removed from the tube port 1400. Other suitable retention methods can also be used, including snap fit or clamshell type devices which can fit over the abutting portions of the sensor 1500 and the tube port 1400. At least a portion of the tubing 1450 may be translucent or transparent to facilitate detection of leaks between the tube port 1400 and the sensor 1500.

Figure 12A:
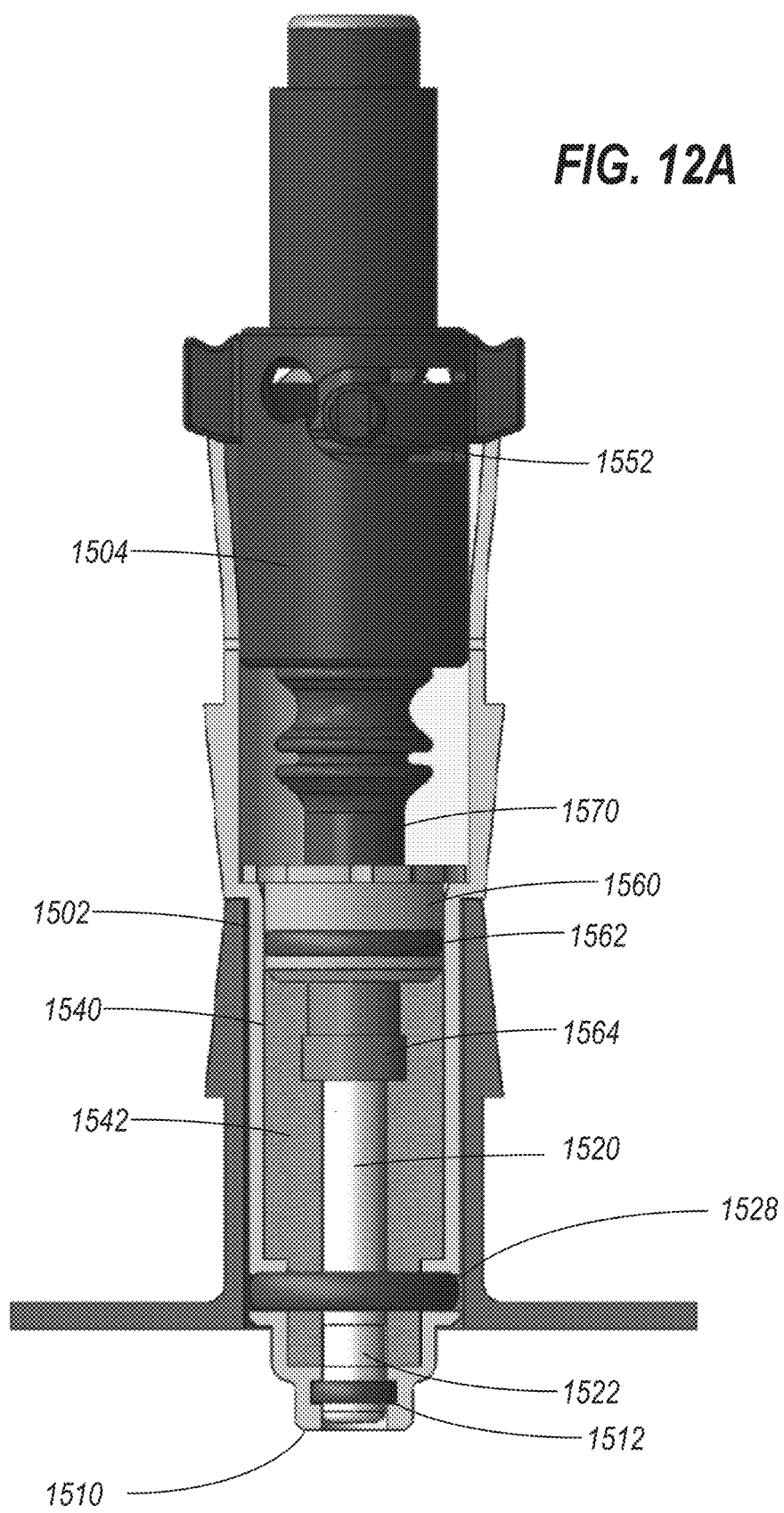
FIGS. 12A and 12B are cutaway figures which illustrate the internal components of the sensor structure of FIG. 11A in a retracted and extended configuration, respectively.
Figure 12B:
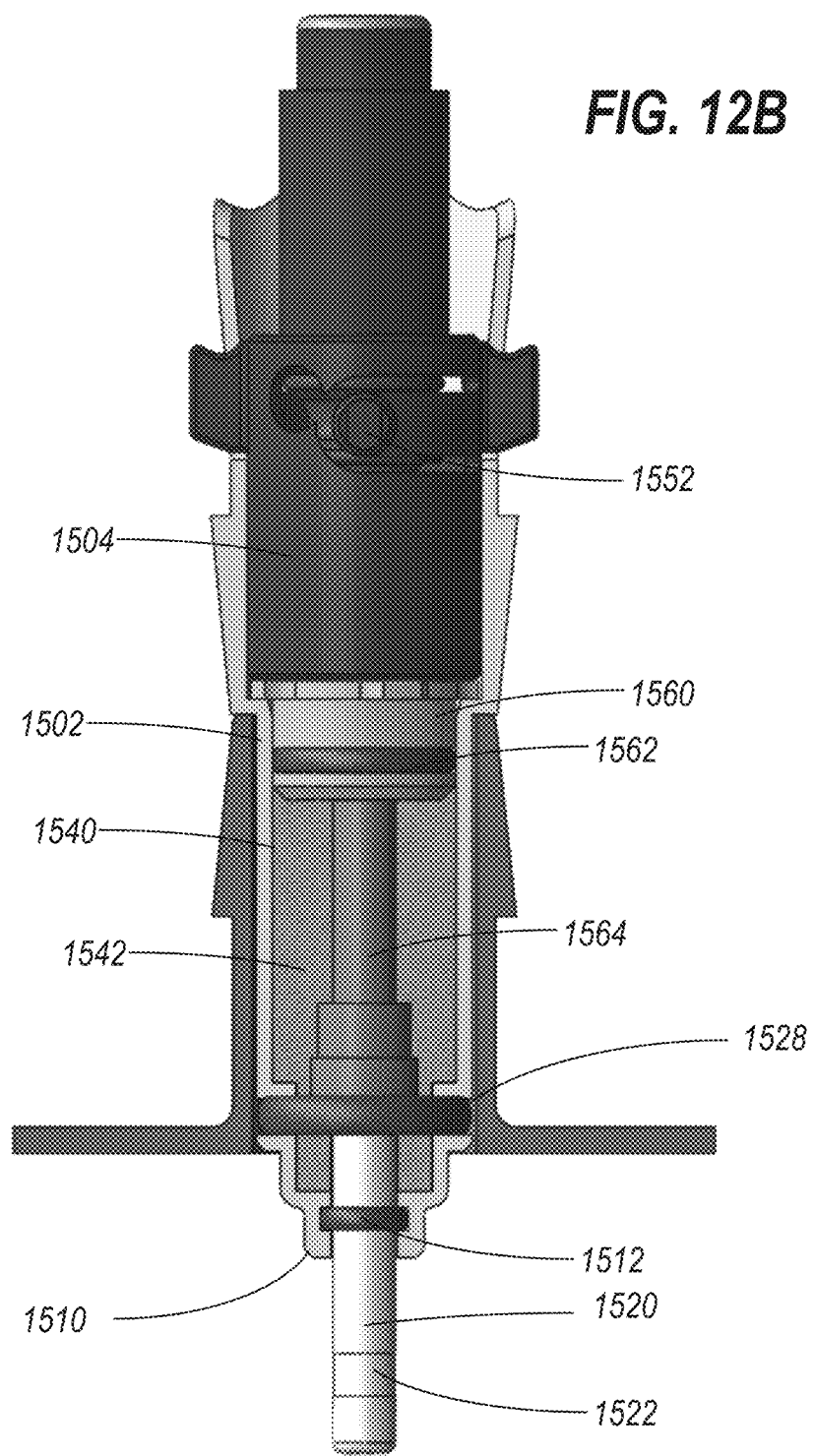

FIGS. 12A and 12B are cutaway figures which illustrate the internal components of the sensor structure of FIGS. 11A to 11C in both a retracted and extended configuration. In FIG. 12A, it can be seen that the distal tip 1510 of the sensor housing 1502 has a smaller cross-sectional area than the remainder of the sensor housing 1502, and that the distal internal gasket 1512 is secured within the region of smaller cross sectional size. By reducing the cross-sectional size of the sensor housing 1502 at the distal tip 1510, the smaller distal internal gasket 1512 can be used to maintain a seal without the need to form a thicker section of the sensor housing wall. In other embodiments, however, the thickness of the wall of the sensor housing near the distal tip 1510 may be increase to provide a similarly-shaped interior space, with a wider outer cross-sectional shape. In addition, the size of the seal formed between the distal internal gasket 1512 and the sidewall of the sensing element 1520 is reduced, decreasing the possibility or the amount of leakage of storage solution 1542 from the storage chamber 1540.

It can also be seen that when the movable component 1504 is in the retracted position, the tip of the sensing element 1520 is pulled back within the space between the distal internal gasket 1512 and the edge of the distal tip 1510 of the sensor housing 1502, which may provide additional protection against damage to the sensor element and possible disruption of the seal between the distal internal gasket and the sensor element. In some embodiments, a protective structure such as a bumper or guard pins could overlie at least a portion of the tip of the sensing element. The use of a blunt protective structure can avoid perforation of a bioreactor bag in a folded position.

The proximal end of the storage compartment 1540 is defined by a plug 1560 including a proximal internal gasket 1562 which cooperates with the internal sidewall of the sensor housing 1502 to retain the storage solution 1542 within the storage compartment 1540. A passage extending through the plug 1560, which may include an internal gasket (not shown) allows a plunger 1564 supporting and retaining the sensing element 1520 to be translated longitudinally through the plug 1560 as the movable component 1504 is moved.

As can be seen in FIG. 12B, when the sensing element 1520 is in an extended position, a portion of the plunger 1564 which was originally located proximal of the plug 1560 is now extending into and in contact with the interior of the storage compartment 1540 and exposed to the storage solution 1542. In order to maintain the sterility of the storage chamber 1540, a bellows structure 1570 located proximal of the plug 1560 define a sterile and compressible area within which a proximal portion of the plunger 1564 is retained when the sensing element 1520 is in an unextended or retracted position.

In some embodiments, the sensing element may be a part of a smart sensor or similar structure, which includes, among other components, a memory circuit. In some embodiments, this memory can also be used to validate the operational history of such a smart sensor. Inadvertent or mistimed movement of the movable element of such a smart sensor that results in retraction of the sensing surface from the process media during the process can compromise the integrity of the sensor measurement and can affect the operation or outcome of a bioprocess with which the sensor is used.

In some embodiments, where feedback from a pH or similar sensor is used to manage a bioprocess, early or delayed exposure of the sensing surface to the process medium can cause the bioprocess to be incorrectly controlled. If a problem occurs with a bioreactor run, it may be necessary to demonstrate the root cause of this issue. By monitoring or recording indications that the sensing element was extended, the operational history of such a sensor can be monitored and preserved.

In some embodiments, the sensor can include a mechanism for detecting movement of the sensing element or another movable component of the sensor relative to the sensor housing. In one embodiment, this movement detection mechanism may include a mechanical contact, a proximity switch, or any other suitable mechanism for detecting or providing an indication of the relative position of a component of the sensor.

In some particular embodiments, movement of the movable component away from a particular position may be detected, while in other embodiments, movement to a particular position or past a particular position may be detected. In some embodiments, multiple detection mechanisms may be included, such as a first detection mechanism configured to detect movement of a component to or away from a first position, and a second detection mechanism configured to detect movement of the component to or away from a second position.

In an embodiment of a sensor structure such as the sensor structure of FIGS. 11A-12B, movement of the sensing element 1520 can be detected via one or more movement detection mechanisms. These movement detection mechanisms need not be located on or adjacent the sensing element itself, but may instead be located, in some embodiments, proximal of the entire sensing element 1520. For example, the detection sensors may be supported by or adjacent another portion of the movable component 1504, as the attachment of the sensing element 1520 to movable component 1504 means that there is a direct correlation between translation of the movable component 1504 and translation of the sensing element 1520 supported by the movable component 1504. Thus the movement and position of the sensing element 1520 can be indirectly but precisely monitored by monitoring the movement or position of another portion of movable component 1504.

Upon detection of movement indicative that the sensing element has been moved relative to the sensor housing, time-stamped information relating to the movement of the sensing element may be written to or otherwise recorded in the memory of the smart sensor. In an embodiment in which the smart sensor is connected to or otherwise in communication with an external instrument, such information may be transmitted to the external instrument or system, where it can be stored in the memory of the external instrument or device. In some embodiments, even a sensor without an included memory can include movement detection mechanisms available to be used by an external instrument to detect and record movement of the sensing element when the sensor is connected to the external instrument. In this way, a log or other record can be generated, indicative of the movement of the sensing element and the times at which that movement occurred.

In embodiments in which the sensor structure is gamma ray sterilized, the exposure to gamma radiation may place constraints on the type of circuitry which can be included in the sensor structure itself. In one embodiment, the sensor structure may include a robust memory chip capable of withstanding gamma radiation, as well as a movement detection mechanism which can be utilized in conjunction with a connected external instrument or other connected instrumentation, such as galvanic contacts which are closed when the sensor is in a particular position. The connected instrument can detect movement of a component of the sensor structure to or away from a given position, and record timestamped information regarding this movement to the memory chip within the sensor structure. In such an embodiment, an event log can be maintained within the robust memory chip included in the sensor structure.

In some embodiments, the connected instrumentation may include a dongle or other component which can be attached to the connector after the bioreactor bag is set up, and which includes circuity which is configured to operate in connection with a hardened memory chip and one or more movement detection mechanisms to record to the hardened memory chip information relating to detected movement. By including this circuitry in a supplemental component, the circuitry in the supplemental component need not be made sufficiently robust to withstand the gamma ray sterilization process. The supplemental component can in some embodiments remain in place when a connection is made to other external instrumentation, such as by connecting the external instrumentation and the supplemental component in series.

In some embodiments, the detection of motion by an external instrument need not be contemporaneous with the occurrence of the motion. For example, in some embodiments, the movement detection mechanism may include a circuit and/or a mechanical component which can be tripped or otherwise altered by movement of a component of the sensor relative to the sensor housing. Such a circuit and/or component may be altered in a manner which can be detected by an external instrument, or directly observed by a user. This alteration may in some embodiments provide an indication of the time at which the movement occurred.

In some devices, a mechanical interlock or similar feature can be used to prevent retraction of a sensing element without operator assistance, to prevent inadvertent termination of process media sensing. Detecting and recording information relating to the timing movement of the sensing element can provide additional protection beyond or in addition to protection provided by a mechanical interlock. The movement record thus generated can be helpful in documenting both abnormal and successful bioreactor runs. This tracking can also provide an additional check as to the proper handling and sterility of a single-use sensor before use.

In some embodiments, the sensor output may also be used to provide an indication of movement of the sensing surface in or out of the storage compartment. If the sensor output is continually or periodically monitored, the smart sensor can detect a deviation from the sensor output corresponding to immersion in the storage medium, and can record, for example, a timestamp or similar information indicative of the insertion time of the sensor. This sensor exposure timestamp or similar information can provide another record of the process timeline.

In some embodiments, the storage solution is a reference solution, such as the reference solution used in the sensing element itself. In other embodiments, the storage solution may be a pH buffered storage solution. Because the storage medium is a sealed compartment, the pH and other characteristics of the storage medium will remain constant while the sensing element is retained within the storage and calibration chamber. At the point of time at which the sensing element is pushed into the process medium, the sensing surface and reference electrode of the sensor are immersed in the process medium, which will have characteristics different than the characteristics of the storage medium. Upon exposure to the process medium, the sensor output will deviate from the substantially constant sensor output which resulted from immersion in the storage medium.

This deviation from the constant sensor output while immersed in the storage medium provides an indication that the sensor has been inserted into the process medium, or that the storage medium has become compromised, and can be used to provide additional validation of both the integrity of the storage compartment and of the time at which the sensor was first extended into the process medium. Because the storage medium will in many embodiments have characteristics which are substantially different from the process medium, retraction of the sensing element into the storage medium can also be detected by a return of the sensor output to a sensor output similar to the substantially constant sensor output which resulted from immersion in the storage medium.

Figure 13A:
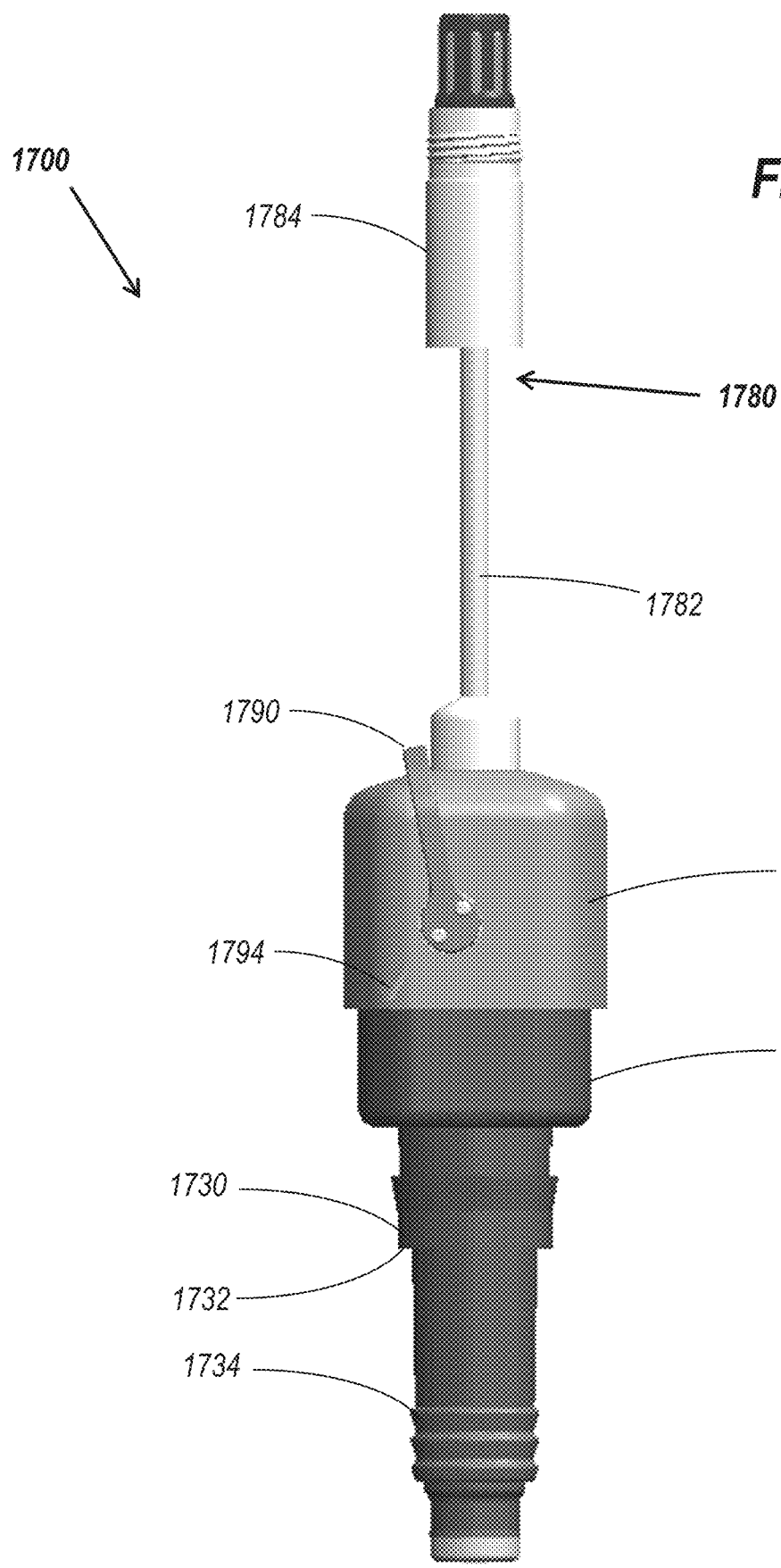
FIG. 13A is a side view of another embodiment of a sensor structure including a sensing element such as the sensing element of FIG. 2 and a storage compartment containing a storage solution, configured to be inserted into a tube port.
Figure 13B:
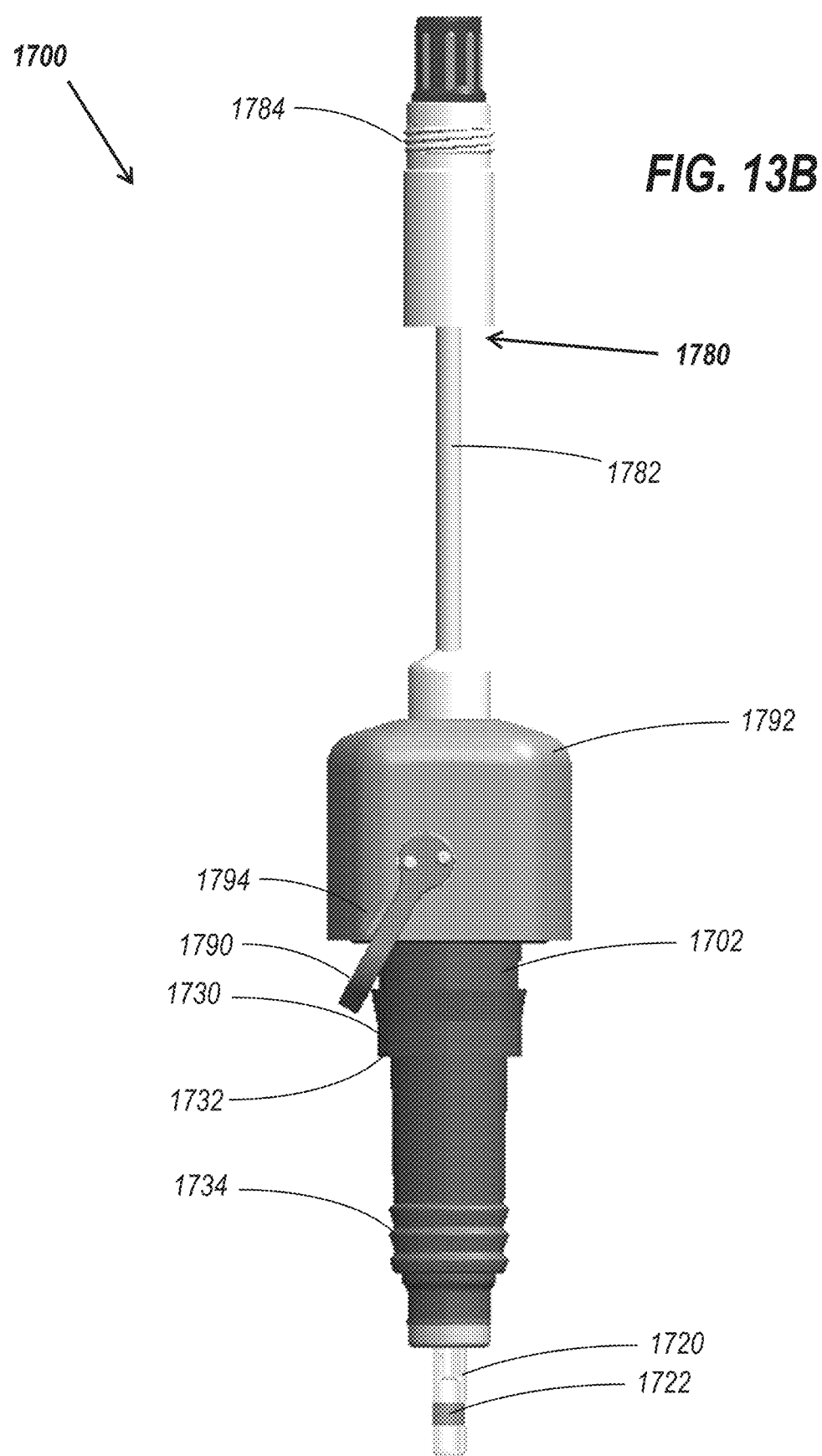
FIG. 13B is a side view of the sensor of FIG. 13A, shown in an extended position.
Figure 14A:
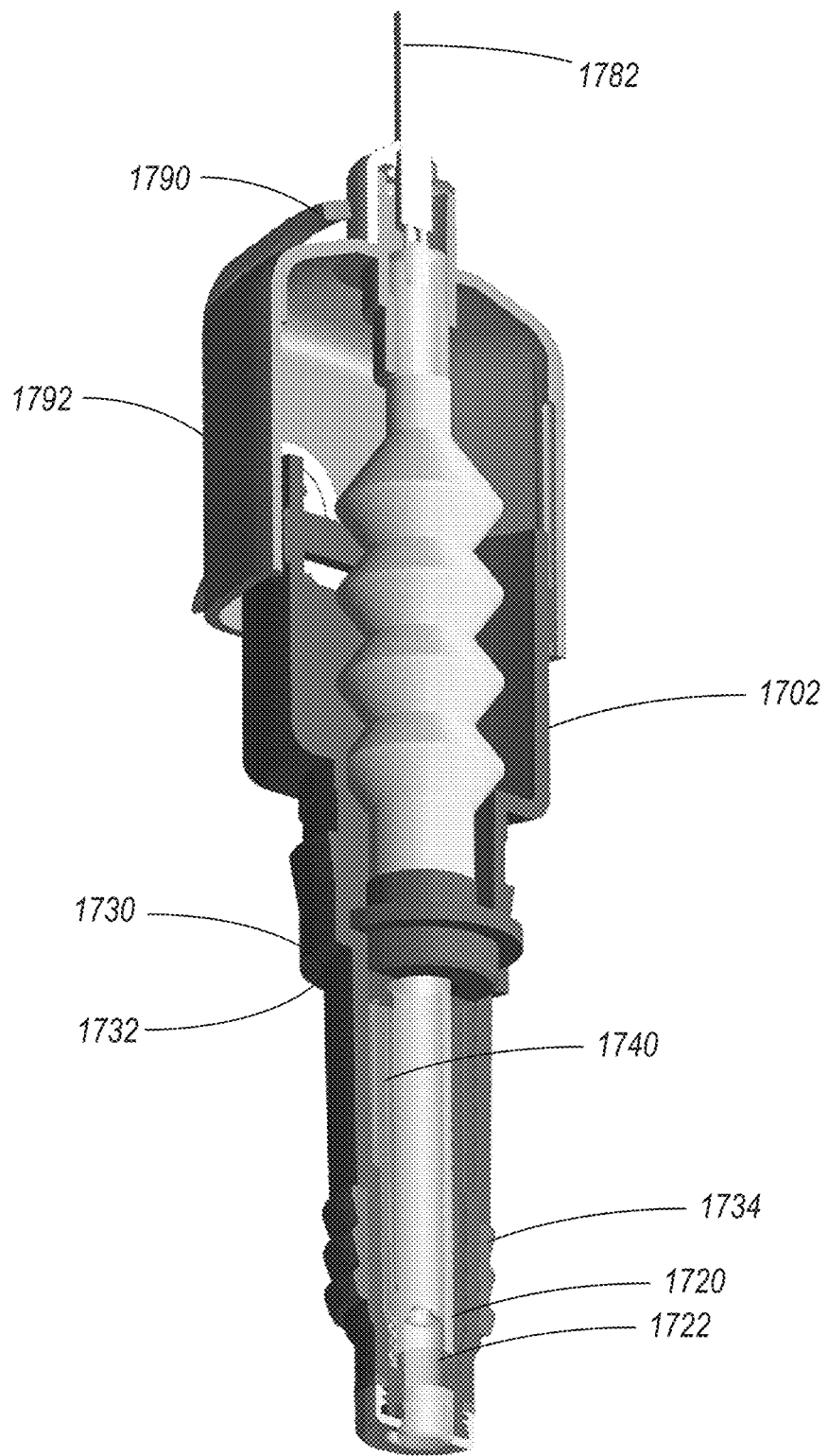
FIG. 14A is a cross-sectional perspective view of the sensor structure of FIG. 13A, shown in a retracted position.
Figure 14B:
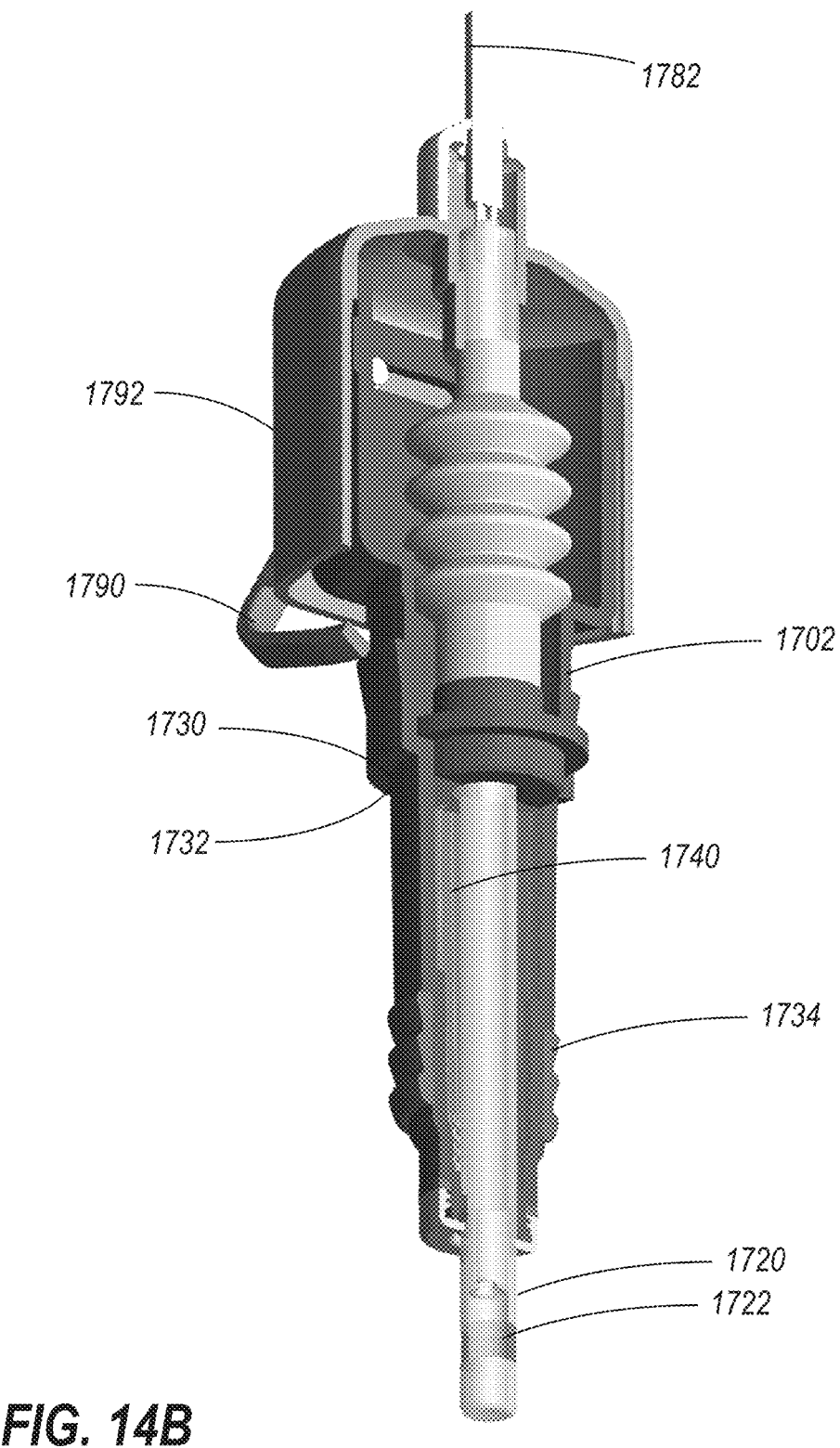
FIG. 14B is a cross-sectional perspective view of the sensor structure of FIG. 13A, shown in an extended position.

FIG. 13A is a side view of another embodiment of a sensor structure including a sensing element such as the sensing element of FIG. 2 and a storage compartment containing a storage solution, configured to be inserted into a tube port. FIG. 13B is a side view of the sensor of FIG. 13A, shown in an extended position. FIG. 14A is a cross-sectional perspective view of the sensor structure of FIG. 13A, shown in a retracted position. FIG. 14B is a cross-sectional perspective view of the sensor structure of FIG. 13A, shown in an extended position.

The sensor structure 1700 is similar to sensor structure 1500 in certain aspects, and like sensor structure 1500, the sensor structure 1700 may be a single-use sensor such as a single-use pH sensor, including a sensor housing 1702 which includes a storage compartment 1740 containing a storage solution. The sensor housing 1502 can be secured relative to a tube port 1400 as shown, or other suitable structure. The sensor structure 1700 includes a movable component which is longitudinally translatable relative to the sensor housing 1702.

The movable component supports a sensing element 1720 having a sensing surface 1722 such as the sensing element 200 of FIG. 2. One or more external gaskets or O-rings can be used to cooperate with the internal surface of a tube port to maintain the integrity of the bioreactor bag in which the tube port is installed, as described below.

A connector 1780 extends from the proximal end of the sensor structure 1700. The connector 1780 differs from the connector 1580 of the sensor structure 1500 in that the connector 1780 includes a length of cabling 1782 extending between the proximal end of the sensing element 1720 and the connector interface 1784 at the proximal end of the connector 1780. In some embodiments, a sensor structure 1700 may be provided with only the connected cabling 1782, and a desired connector interface for use with a particular external instrument or system may be attached at a later point in time.

The interface mechanism for translating the movable component of the sensor structure 1700 also differs from that of the sensor structure 1500. As can be seen, the interface mechanism of sensor structure 1700 includes a throw lever 1790, comprising a generally U-shaped handle operably coupled at the end of both arms to the upper housing section 1792, which in the illustrated embodiment serves as the movable component of the sensor structure 1792 and supports the sensing element 1720 near the proximal end of the sensing element 1720. The throw lever 1790 may facilitate operation of the sensor structure 1700 while a user is wearing gloves, or when there are other impediments to interaction with the sensor structure.

The throw lever 1790 is movable between a first position, shown in FIG. 12A, in which the throw lever 1790 lies against or adjacent a proximal section of the upper housing section 1792, and a second position, shown in FIG. 12B, in which the throw lever 1790 lies against or adjacent a distal section of the upper housing section 1792. The throw lever 1790 is operably coupled via a suitable mechanical linkage, cam surfaces, or another suitable mechanical arrangement to the movable component of the sensor structure 1700. Raised features 1794 on the surface of the upper housing section 1792 may cooperate with the throw lever 1790 to provide some resistance against inadvertent movement away from a desired position of the throw lever 1790.

The shape of the upper housing section 1792, and in particular the generally cylindrical sidewall section of the upper housing section 1792 underlying the throw lever 1790, cooperates with the shape of the throw lever 1790 to constrain the positions to which the throw lever 1790 can be moved. Because the throw lever 1790 is operably coupled to the movable component of the sensor structure 1700, constraint on the travel range of the throw lever 1790 constrains the longitudinal translation of the movable component, which in turn constrains the longitudinal translation of the supported sensing element 1720.

The shape of the distal section of the sensor housing 1702 also differs from the shape of the distal section of the sensor housing 1502 of the sensor structure 1500. In contrast to the sensor housing 1502, which includes a single flared section 1530 of the sensor housing 1502, the sensor housing 1702 includes a proximal flared section 1730 having a distal surface 1732 which can abut a proximal surface of a tube port, but also includes a ridged section 1734 formed from a resilient material such as silicone rubber and having ridges of increasingly larger diameter in the proximal direction. The flexible ridged section can abut a internal surface of a tube port to ensure a fluid seal will be formed despite variations in the internal cross-sectional size of the tube port, or imperfections in the interior surface of the tube port.

Figure 15:
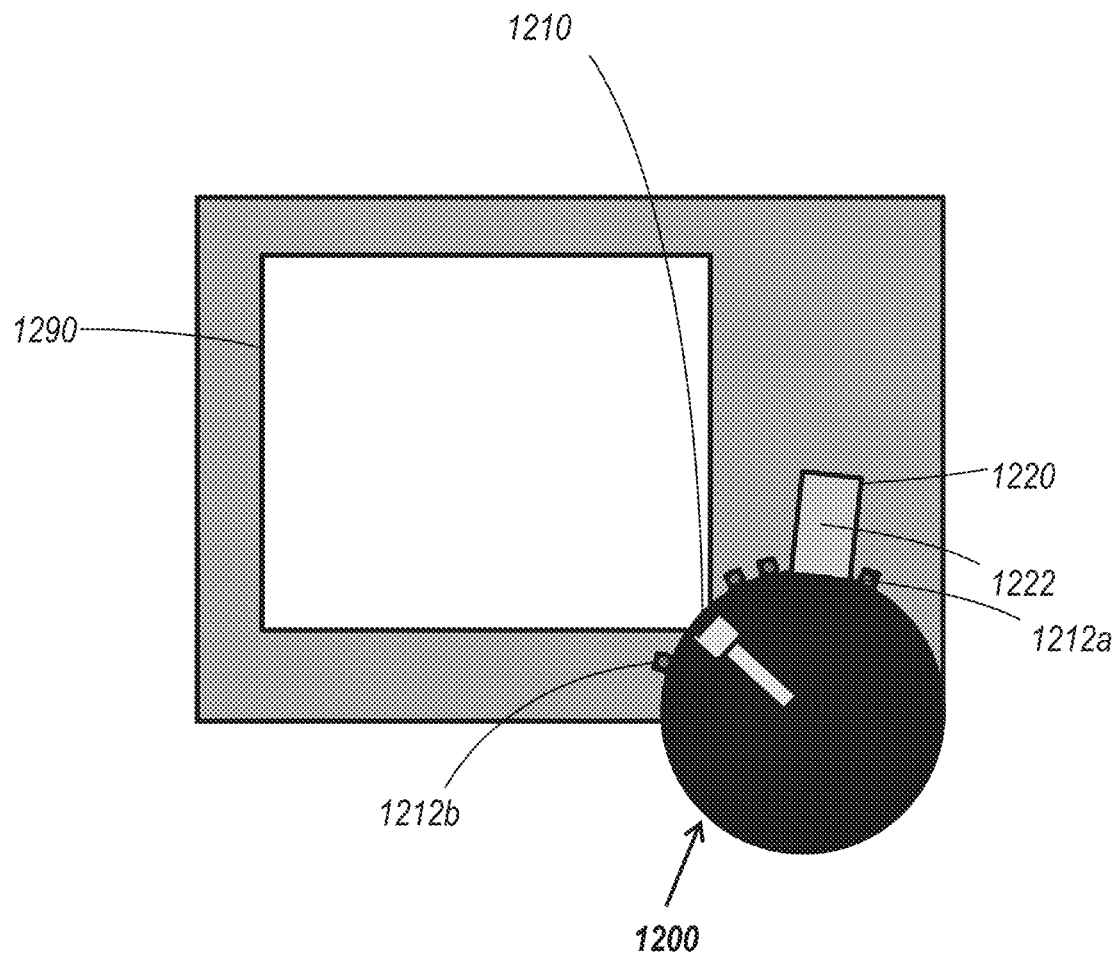
FIG. 15 is a top cross-sectional view schematically illustrating an embodiment of a sensor structure including a sensing element which can be rotated to expose a sensing surface to a process medium.

In other embodiments, movement of the sensing element to selectively expose the sensing surface to the process medium and to the storage/calibration medium may include rotation of the sensing element, in addition to or in place of translation of the sensing element in a given direction. FIG. 15 is a top cross-sectional view schematically illustrating a sensor structure including a sensing element which can be rotated to expose an active portion of the sensing surface to a process medium. The sensor structure includes a cylindrical sensing element 1200 including a sensing surface 1210 which does not extend around the entire circumference of the sensing element 1200. The sensing element 1200 can also include a half-cell element lead and an internal electrolyte, as discussed elsewhere herein, and may also include an integrated reference electrode. In some embodiments, the sensing surface 1210 extends around less than half the circumference of the sensing surface 1200, although in other embodiments it can extend around substantially less than half the circumference of the sensing element 1200, as shown in FIG. 15.

The surface of the sensing element 1200 is in contact with a first sealing element 1212*a* and a second sealing element 1212*b*. The first sealing element 1212*a* cooperates with the surface of the sensing element 1200 to seal a storage compartment 1220 containing a storage/calibration medium 1222. The second sealing element extends around an aperture in fluid communication with a space 1290 which can be filled with or otherwise exposed to a process medium. By rotating the sensing element 1200 relative to the sealing elements 1212*a* and 1212*b*, the sensing surface 1210 of the sensing element 1200 can be moved between a first position in which it is in fluid communication with the storage/calibration medium 1222 of the storage compartment 1120, and a second position in which the sensing surface 1210 is circumscribed by the second sealing element 1212*b* to allow the sensing surface 1210 to be exposed to the process medium in the space 1290.

Regardless of the direction of rotation or translation of the sensing element, a fluid-tight seal can be maintained during movement of the sensing element as long as the portion of the sensing element in contact with a sealing element has a substantially constant shape. The portions of the sensing element which will not contact the sealing element need not have a substantially constant shape. Thus, portions of the sensing element 200 of FIG. 2 which are located sufficiently proximal or distal the sensing surface (or other portions which will contact a sealing element) can have a varying cross-sectional shape. Similarly, only a portion of the sensing element 1200 of FIG. 15 may have an outer surface in the shape of a circular arc, while the other surfaces may be any suitable shape, so long as the sealing elements do not contact those portions of the sensing element during movement of the sensing element. Similarly, a sealing element may be configured to maintain a substantially fluid-tight seal when in contact with a portion of a sensing element with a surface having a particular surface profile or shape. As long as the profile of the portion of the sensing element contacting the fluid-tight seal has a substantially constant surface profile or shape, the substantially fluid-tight seal can be maintained during translation and/or rotation of the sensing element, due to the sealing element cooperating with the surface of the sealing element.

Mechanical stops or other movement-constraining structures or devices may be included to prevent the sensing element from being translated to a position where the shape of the section of the sensing element in contact with the sealing element changes. In addition, some variance in shape may be tolerated due to the tolerance of the sealing element.

Figure 16A:
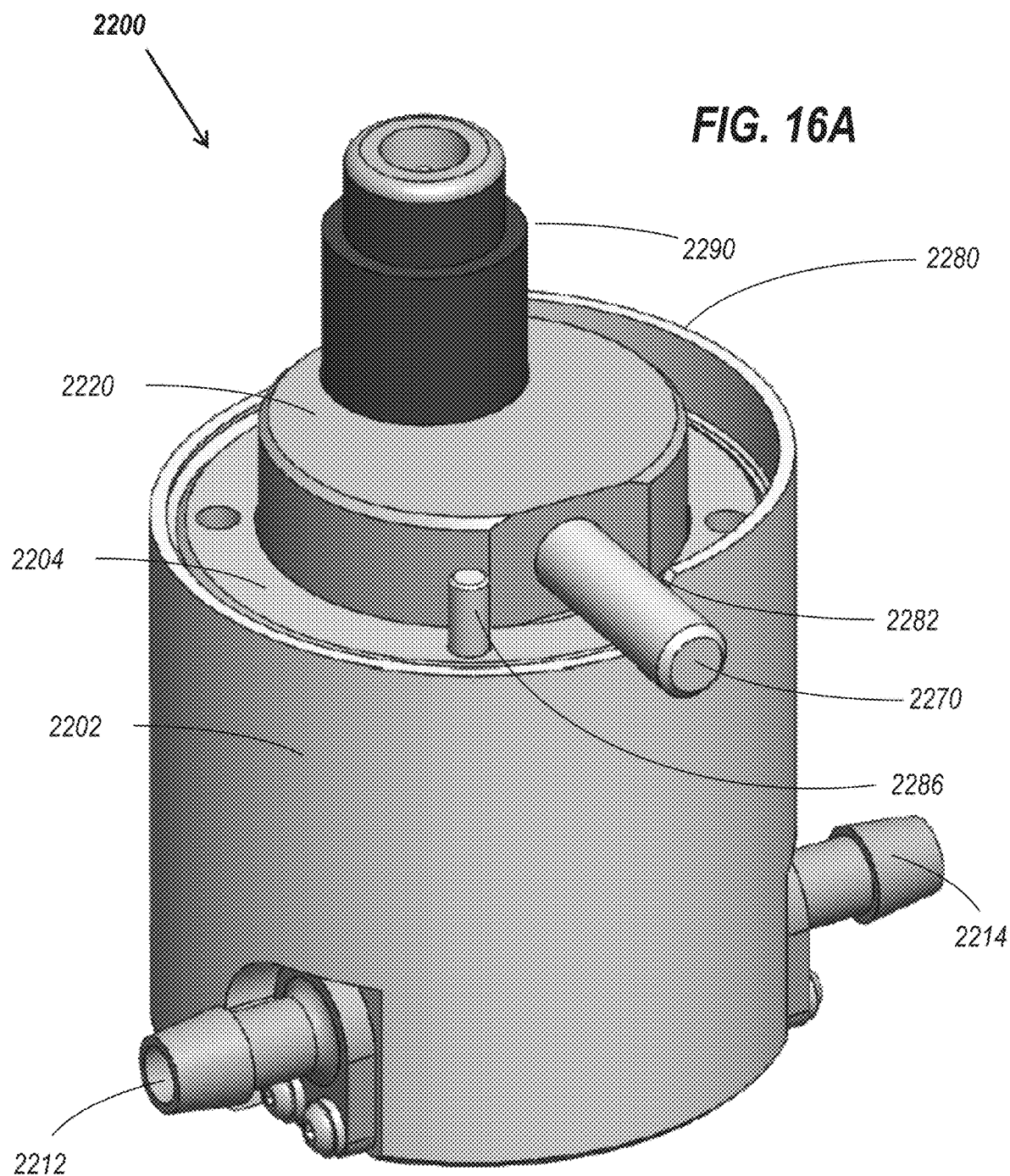
FIG. 16A is a perspective view of another embodiment of a sensor structure including a sensing element configured for use in a flow-through arrangement and comprising a storage compartment containing a calibration solution.
Figure 16C:
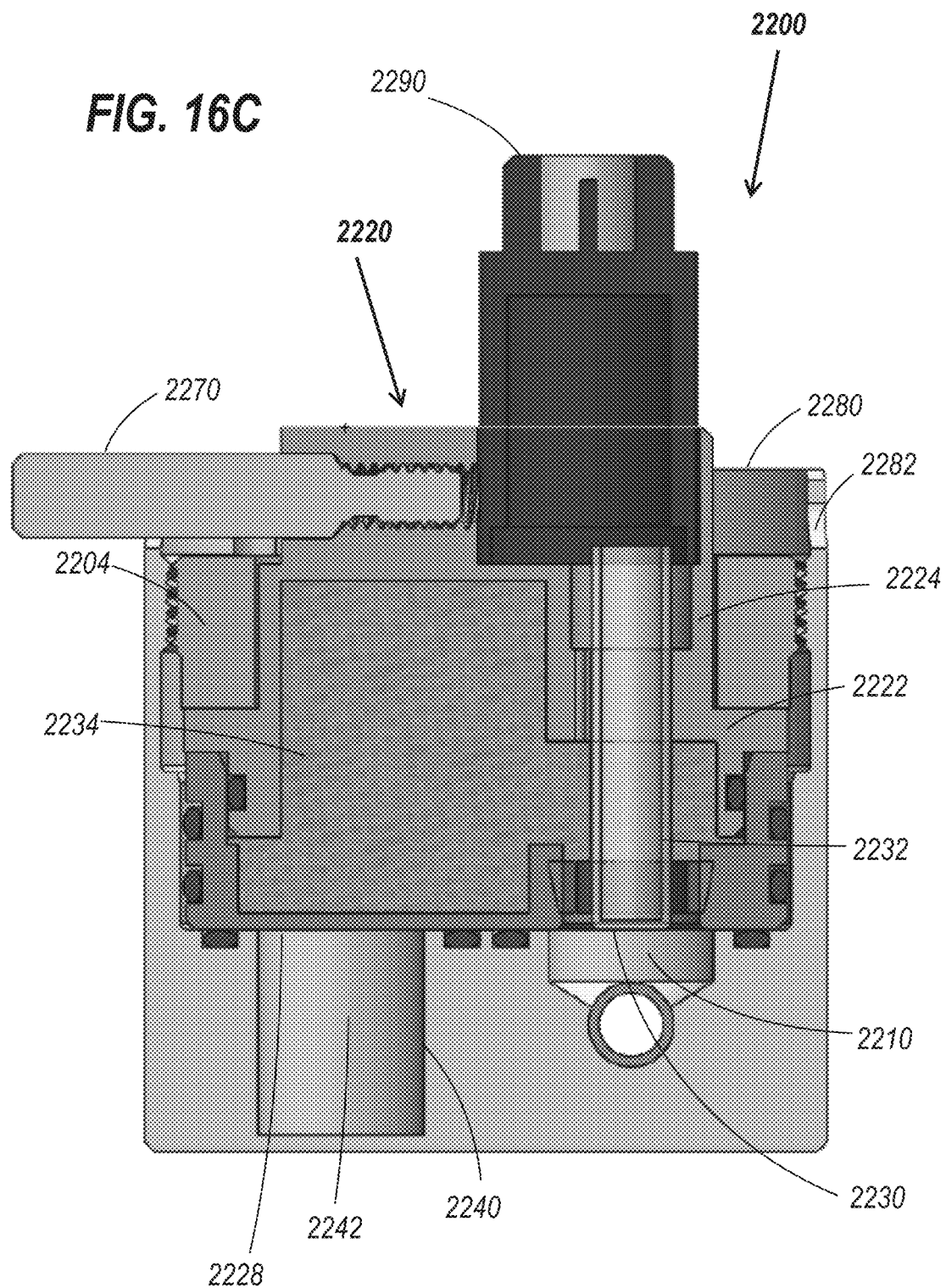
FIG. 16C is a side cross-sectional view of the sensor structure of FIG. 16A, with the sensor shown in a position in which the sensing element is exposed to an inline flow-cell chamber.

FIG. 16A is a perspective view of another embodiment of a sensor structure including a sensing element configured for use in a flow-through arrangement and comprising a storage compartment containing a storage solution. FIG. 16B is a side cross-sectional view of the sensor structure of FIG. 16A, with the sensor shown in a position in which the sensing element is exposed to storage solution. FIG. 16C is a side cross-sectional view of the sensor structure of FIG. 16A, with the sensor shown in a position in which the sensing element is exposed to an inline flow-cell chamber.

The sensor structure 2200 comprises a rotatable sensor drum 2220 secured within a sensor housing 2202. The sensor housing 2202 comprises an inlet 2212 and an outlet 2214. The inlet 2212 and the outlet 2214 are in fluid communication with one another via the inline flow-cell chamber 2210, which includes an upper aperture adjacent the facing lower surface of the rotatable sensor drum 2220. Although referred to as an inlet 2212 and an outlet 2214, the flow direction into and out of the inline flow-cell chamber 2210 may in some embodiments go in either direction The sensor structure 2200 includes a connector 2280 extending upwards from the rotatable sensor drum 2200. This connector 2280 can be used to place the sensor structure in communication with an external instrument or other system. In the illustrated embodiment, the connector 2290 is offset from an axis of rotation of the rotatable sensor drum 2220 but in other embodiment, the connector 2280 may be aligned with the axis of rotation of the rotatable sensor drum 2220.

The rotatable sensor drum 2220 in the illustrated embodiment includes a wider lower portion 2222 of larger cross-sectional area than a narrower upper neck portion 2224. A collar 2204 secured to the sensor housing 2202 and having a central aperture that is substantially equal in cross-sectional size to the cross-sectional size of the upper neck region 2224 and smaller than the cross-sectional size of the lower portion 2222 of the sensor drum 2220 retains the rotatable sensor drum 2220 in place. Because the central aperture of the collar 2204 is aligned with the axis of rotation of the sensor drum 2220, and because the portions of the sensor drum retained within the sensor housing 2204 are rotationally symmetric, the sensor drum 2220 can be rotated within the sensor housing 2202. In the illustrated embodiment, a collar gasket 2208 provides a seal below the threaded connections between the collar 2204 and the sensor housing 2202.

In the illustrated embodiment, an outwardly extending lever 2270 is attached to the sensor drum 2220 to facilitate rotation of the sensor drum 2220. In other embodiments, the sensor drum may be rotated without the lever 2270, or another suitable mechanism may be provided to facilitate rotation of the sensor drum, such as mechanical features which may be gripped by a user, or which may engage another mechanism used to rotate the sensor drum 2220.

The lever 2270 cooperates with other features of the sensor housing 2202 to constrain rotation of the sensor drum. In the illustrated implementation, the sensor housing 2202 comprises a raised wall 2280 extending around a portion of the sensor housing 2202 and extending into the swept area of the lever 2270. In the illustrated embodiment, the lateral edges of the wall 2280 are complementary with the shape of the lever 2270 such that the wall 2280 defines a first rotational position of the sensor drum 2220 when the lever 2270 is in contact with a first lateral edge 2282 of the wall 2280 and a second rotational position of the sensor drum 2220 when the lever 2270 is in contact with a second lateral edge 2284 of the wall 2280.

One or more pins 2286 can be used to constrain movement of the lever 2270, such as retaining the lever 2270 in one of the first or second positions adjacent a lateral edge of the wall 2280. The pins 2286 may be removable or may be spring loaded or otherwise biased into the swept area of the lever 2270, and movable out of the swept area to allow the lever 2270 to pass thereby when desired.

FIG. 16B is a cross-sectional view illustrating the sensor structure 2200 in a first configuration, where the sensor drum 2220 is in a first position. In the first position, the flat sensing surface 2230 generally flush with the base 2228 of the rotatable sensor drum 2220 and exposed at the base 2228 of the rotatable sensor drum 2220 is aligned with a storage and/or calibration chamber 2240 including a storage medium 2240 to which the flat sensing surface 2230 is exposed when the sensor structure is in the first configuration. The flat sensing surface 2230 serves as the sensing surface of the sensor structure 2200, allowing calibration of the sensor structure 2200 when the sensor structure 2200 is in this first calibration.

The sensor drum 2220 also contains the remainder of the sensing element of the sensor structure 2200. Unlike the sensing element of FIG. 2, for example, the flat sensing surface 2320 of the sensor 2232, a combination pH electrode. An internal chamber within the sensor drum 2220 contains a reference solution 2234 to which the reference electrode of the sensor 2232 of the sensing element is exposed. An electrode gasket 2236 surrounding the flat sensing surface 2230 prevents leakage of the reference solution 2234 through the base 2228 of the sensor drum 2220 and an internal gasket 2238 prevents leakage of the reference solution 2234 between other components of the sensor drum 2220 joined together to define the internal chamber of the sensor drum 2220.

The portion of the base 2228 overlying the inline flow-cell chamber 2210 cooperates with the portion of the sensor housing 2204 surrounding the inline flow-cell chamber 2210 and with the outlet gasket 2218 to allow process media flowing through the inline flow-cell chamber 2210 to pass through the inline flow-cell chamber 2210 without interference or leakage.

In FIG. 16C, the sensor drum has been rotated to expose the flat sensing surface 2230 to the inline flow-cell chamber 2210, placing the sensing surface of the sensing element of the sensor structure 2200 in fluid communication with the inline flow-cell chamber 2210, in a second configuration of the sensor structure 2220. The base 2228 of the sensor drum 2220 seals the storage medium 2242 within the storage compartment 2240 when the sensor component 2200 is in this second configuration.

As discussed above, rotation of the sensor drum from the first position to the second position may include moving the lever 2270 from a first position in which it abuts a first lateral end of the wall 2280 to a second position in which it abuts the second lateral end of the wall 2280. The wall 2280 may thus define the complete travel range of the sensor drum 2220, with the first and second positions of the sensor drum corresponding to the edges of this maximum travel range.

The relative positioning between the storage chamber 2240 and the inline flow-cell chamber 2210 may correspond to the arc defined by the wall 2280. The storage chamber 2240 and the inline flow-cell chamber 2210 are located substantially the same distance laterally outward of the axis of rotation of the sensor drum 2220, so that the flat sensing surface 2230 can be selectively exposed, through rotation of the sensor drum 2220, to both the storage chamber 2240 and the inline flow-cell chamber 2210.

In the illustrated embodiment, the travel range of the sensor drum is roughly 180 degrees, and the storage chamber 2240 and the inline flow-cell chamber 2210 are located on opposite sides of the axis of rotation of the sensor drum 2220. In an embodiment in which the storage chamber 2240 and the inline flow-cell chamber 2210 are located at some other angle to one another, the shape of wall 2280 may be adjusted so that it defines a matching arc. In some embodiments, the entire wall 2280 need not be included, as long as features defining stops for the rotation of the sensor drum are included.

Note that, although the figures depict the sensor structure 2200 in an orientation in which the axis of rotation of the sensor drum 2220 is vertical, the sensor structure 2220 can in use be oriented in a position such as a position in which the axis of rotation of the sensor drum 2220 is horizontal or canted at another angle to the vertical. In such a horizontal configuration, for example, contact between the storage medium 2242 within the storage compartment 2240 and the flat sensing surface 2230 can be ensured.

In an embodiment in which a movement detection mechanism is included in the sensor structure, the movement detection mechanism may be supported by or attached to at least one of the lever or wall. Like the 1:1 translation of a longitudinally translatable component supporting the sensor element, the angular rotation of the lever will correspond to identical angular rotation of the sensor drum and the included sensing surface, and detection of rotational movement anywhere on the sensor drum or attached structures will correspond to rotational movement of the sensor drum.

In the foregoing description, specific details are given to provide a thorough understanding of the examples. However, it will be understood by one of ordinary skill in the art that the examples may be practiced without these specific details. Certain embodiments that are described separately herein can be combined in a single embodiment, and the features described with reference to a given embodiment also can be implemented in multiple embodiments separately or in any suitable subcombination. In some examples, certain structures and techniques may be shown in greater detail than other structures or techniques to further explain the examples.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A sensor structure, comprising:
   a storage compartment configured to retain a storage medium therein;
   a sensing element extending through an aperture in the compartment and comprising a sensing structure, a distal end of the sensing structure located proximal a distal end of the sensing element, the sensing element reversibly movable between a first position in which the sensing structure is in fluid communication within the storage compartment and a second position in which the sensing structure is not in fluid communication with the storage compartment, a proximal portion of the sensing element or of a movable component connected to the sensing element being located proximal and outside of the storage compartment when the sensing element is in the first position, the proximal portion located within the storage compartment when the sensing element is in the second position, the sensing element comprising a sensing surface substantially flush with adjacent surfaces of the sensing element, the sensing element comprising a section of substantially constant cross-sectional shape extending between a point proximal the proximal end of the sensing surface and a point distal the distal end of the sensing surface;
   a sealing element disposed at least partially within the aperture and configured to engage a surface of the sensing element to provide a seal inhibiting fluid flow in or out of storage compartment through the aperture; and
   a sterilizable and compressible compartment proximal the storage chamber and configured to retain the proximal portion when the sensing element is in the first position to maintain the sterility of the storage compartment when the proximal portion is moved into and out of the storage compartment.

2. The sensor structure of claim 1, wherein the sensing element comprises a pH sensor.

3. The sensor structure of claim 1, wherein the sensing structure is in electrical communication with a reference electrode.

4. The sensor structure of claim 1, wherein the storage medium is configured to be used as a calibration medium for the sensing element.

5. The sensor structure of claim 1, wherein translating the sensing element between the first position and the second position does not displace a substantial amount of the storage solution from the storage compartment, and does not expose the interior of the storage compartment.

6. The sensor structure of claim 1, additionally comprising a second sensing element extending parallel to the first sensing element, wherein the second sensing element extends through a second aperture in the storage compartment and engages with a second sealing element disposed at least partially within the second aperture to provide a seal inhibiting fluid flow in or out of storage compartment through the second aperture.

7. The sensor structure of claim 1, wherein the storage compartment comprises a first chamber and a second chamber, the sensing element extending through both the first chamber and the second chamber, wherein the sensing structure of the sensing element is within the first chamber when the sensing element is in the first position, and wherein the sensing element is longitudinally translatable to a third position in which the sensing structure is located within the second chamber, wherein the first chamber retains the storage solution, and wherein the second chamber retains a calibration medium, the calibration medium having a pH which is different from the pH of the storage solution.

8. The sensor structure of claim 1, additionally comprising:
   a movement detection mechanism configured to detect movement of the sensing element relative to the storage compartment, wherein the movement detection mechanism is configured to provide an indication of the time at which the detected movement occurred; and
   a memory chip configured to record a timestamp movement of the sensing element relative to the storage compartment.

9. The sensor structure of claim 1, wherein the sensing structure comprises a pH probe comprising a reference half-cell chamber and a measuring half-cell chamber, a sensing surface of the sensing structure comprising a glass pH electrode in fluid communication with the measuring half-cell chamber, the glass pH electrode located distal a distal end of the reference half-cell chamber.

10. The sensor structure of claim 1, wherein the sensor structure additionally comprises a bellows structure defining the sterilizable and compressible compartment.

11. The sensor structure of claim 1, wherein the sensor structure additionally comprises a sterile barrier defining the sterilizable and compressible compartment.

12. The sensor structure of claim 1, wherein the sensing structure comprises a pH probe comprising a reference half-cell chamber and a measuring half-cell chamber, a sensing surface of the sensing structure comprising a glass pH electrode in fluid communication with the measuring half-cell chamber, the glass pH electrode located distal a distal end of the reference half-cell chamber.

13. The sensor structure of claim 1, wherein the sensing element comprises a pH probe comprising a distal section comprising a substantially constant cross-sectional shape, the distal section comprising:
   at least a portion of a reference half-cell chamber;
   at least a portion of a measuring half-cell chamber;
   an inert distal tip; and
   a sensing surface in fluid communication with the measuring half-cell chamber and located distal a distal end of the reference half-cell chamber.

14. The sensor structure of claim 1, wherein the sealing element comprises an aperture extending therethrough, a distal tip of the sensing element being positioned distal the sealing element when the sensing element is in the first position.

15. The sensor structure of claim 14, wherein the sealing element comprises an O-ring.

16. The sensor structure of claim 14, wherein the sealing element comprises a gasket.

17. The sensor structure of claim 1, wherein a distal portion of the sealing element is exposed to the exterior of the sensor structure.

18. The sensor structure of claim 1, wherein reversibly moving the sensing element between the first and second positions selectively exposes the sensing structure to a process medium on a distal side of the sealing element while maintaining the seal inhibiting fluid flow in or out of storage compartment through the aperture.

19. A sensor structure, comprising:
   a storage compartment configured to retain a storage medium therein;
   a sealing element disposed at least partially within an aperture in the storage compartment, the sealing element comprising an aperture extending therethrough;

a sensing element extending through the aperture in the sealing element, the sealing element configured to engage a surface of the sensing element to provide a seal inhibiting fluid flow in or out of storage compartment through the aperture in the storage compartment, the sensing element comprising a sensing surface substantially flush with adjacent surfaces of the sensing element, a distal end of the sensing surface located proximal a distal end of the sensing element, the sensing element comprising a section of substantially constant cross-sectional shape extending between a point proximal the proximal end of the sensing surface and a point distal the distal end of the sensing surface, the sensing element reversibly movable between:

a first position in which the sensing structure is in fluid communication within the storage compartment and a distal end of the sensing element is located distal of the sealing element, and a second position in which the sensing structure is located distal of the sealing element, a proximal portion of the sensing element or of a movable component connected to the sensing element being located proximal and outside of the storage compartment when the sensing element is in the first position, the proximal portion located within the storage compartment when the sensing element is in the second position; and a sterilizable and compressible compartment proximal the storage chamber and configured to retain the proximal portion when the sensing element is in the first position to maintain the sterility of the storage compartment when the sensing element is moved between the first and second positions to move the proximal portion into and out of the storage compartment.

* * * * *